(12) United States Patent
Geromanos et al.

(10) Patent No.: US 9,734,996 B2
(45) Date of Patent: Aug. 15, 2017

(54) SYSTEM AND METHOD FOR ENHANCING CHARGE-STATE DETERMINATION IN ELECTROSPRAY MASS SPECTROMETRY

(71) Applicant: Waters Technologies Corporation, Milford, MA (US)

(72) Inventors: Scott J Geromanos, Middletown, NJ (US); Steven J Ciavarini, Natick, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 15/318,321

(22) PCT Filed: Jun. 12, 2015

(86) PCT No.: PCT/US2015/035540
§ 371 (c)(1),
(2) Date: Dec. 12, 2016

(87) PCT Pub. No.: WO2015/191993
PCT Pub. Date: Dec. 17, 2015

(65) Prior Publication Data
US 2017/0117123 A1    Apr. 27, 2017

Related U.S. Application Data

(60) Provisional application No. 62/011,665, filed on Jun. 13, 2014.

(51) Int. Cl.
*H01J 49/00*    (2006.01)
*G01N 30/86*    (2006.01)

(52) U.S. Cl.
CPC ...... *H01J 49/0036* (2013.01); *G01N 30/8675* (2013.01)

(58) Field of Classification Search
CPC .................... H01J 49/0036; G01N 30/8675
(Continued)

(56) References Cited

U.S. PATENT DOCUMENTS

2012/0259557 A1   10/2012   Gorenstein et al.
2012/0259577 A1   10/2012   Ganyi
(Continued)

*Primary Examiner* — Michael Maskell
(74) *Attorney, Agent, or Firm* — Diederike & Whitelaw, PLC

(57) ABSTRACT

A method of mass spectrometry comprises ionizing a sample and obtaining mass spectral data relating to a plurality of ion detection events. The method then comprises applying match tolerances for mass to charge ratio (m/z), chromatographic retention time ($t_r$), and ion mobility drift time ($t_d$), to the ion detection events in order to determine possible charge state connections. The method also comprises constructing a tentative isotope chain and querying ion detection events for a match to the tentative isotope chain. Once a tentative isotope chain has been constructed, the method further comprises determining a corresponding theoretical molecular mass and a corresponding theoretical isotopic distribution, querying one or more lookup tables and returning one or more parameters (New X, New X', Δ New X') related to the fractional mass to charge ratio ($f_{m/z}$) and at least one of: ion mobility drift time ($t_d$); and nominal mass to charge ratio ($N_{m/z}$), of the ion detection events, and using the one or more parameters (New X, New X', Δ New X') to determine a unique charge state of the ions.

20 Claims, 29 Drawing Sheets

(58) Field of Classification Search
USPC .......................................... 250/281, 282, 288
See application file for complete search history.

(56) References Cited

U.S. PATENT DOCUMENTS

2013/0282293 A1* 10/2013 Geromanos ........ G01N 33/6848
702/19
2013/0299688 A1* 11/2013 Balogh ................. H01J 49/168
250/282

* cited by examiner

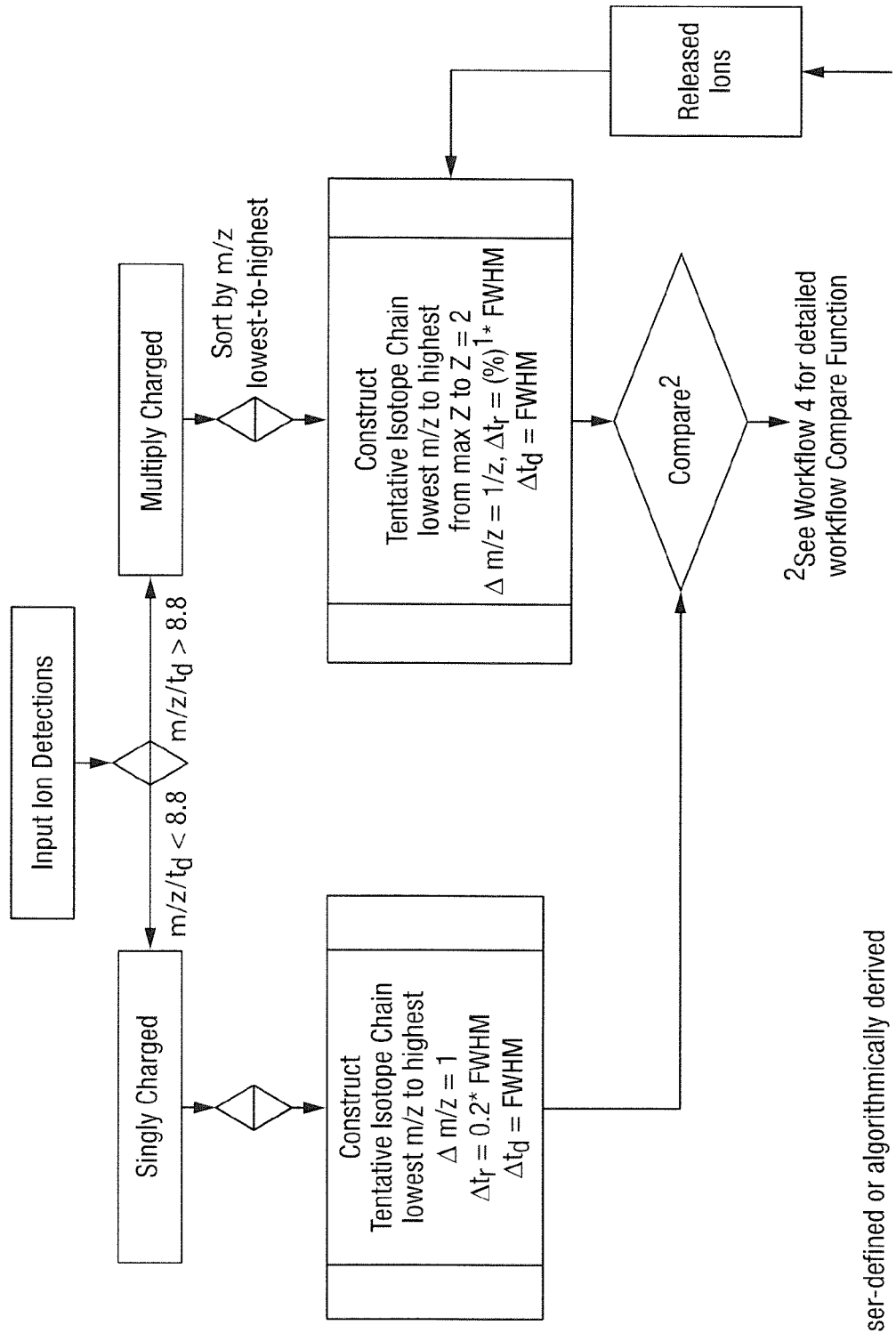
Fig. 2 Create Precursor Charge Groups (isotope clusters)

Channel 1
Low-Energy (Survey) HD-MS$^E$ Ion Detections

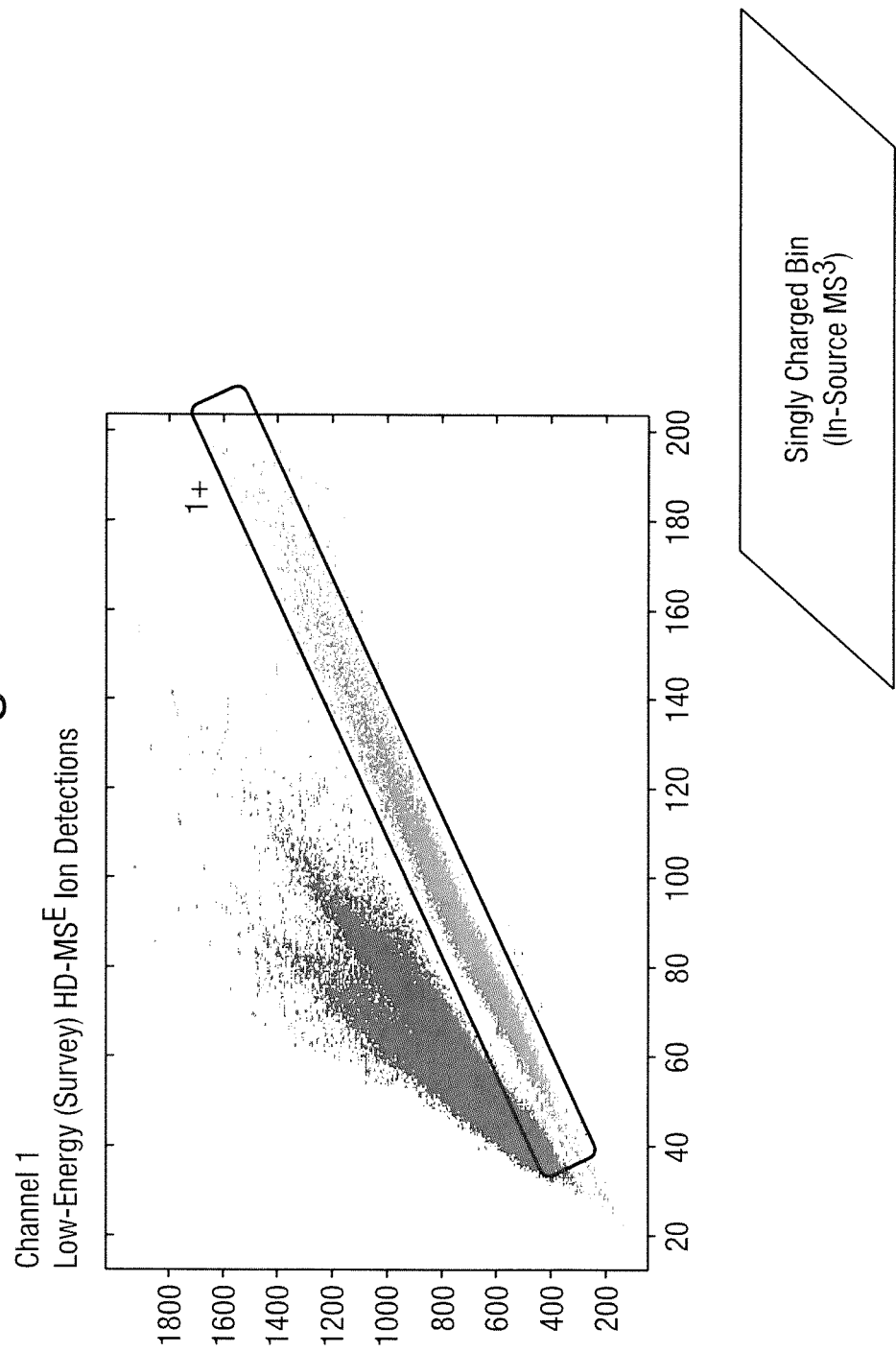

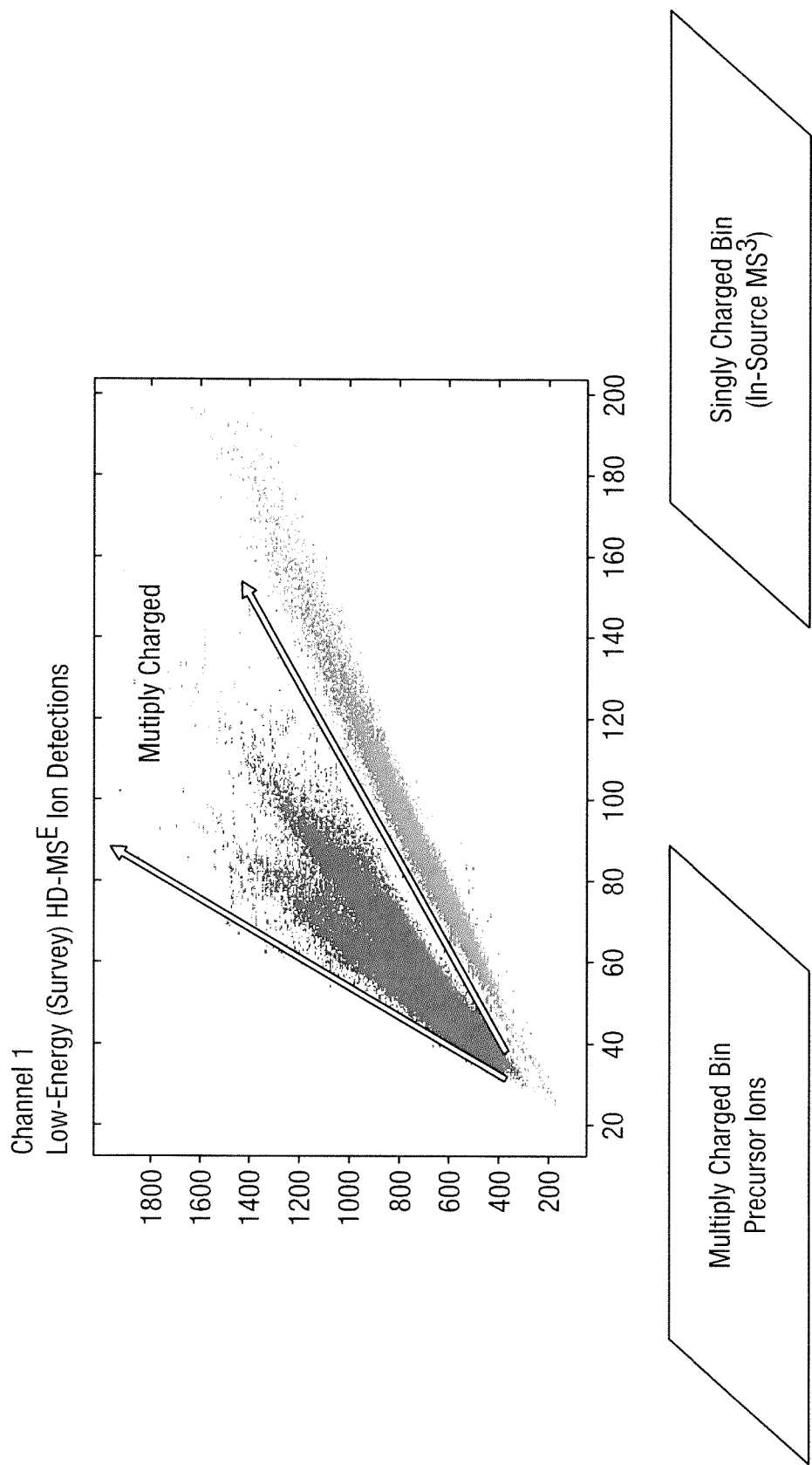

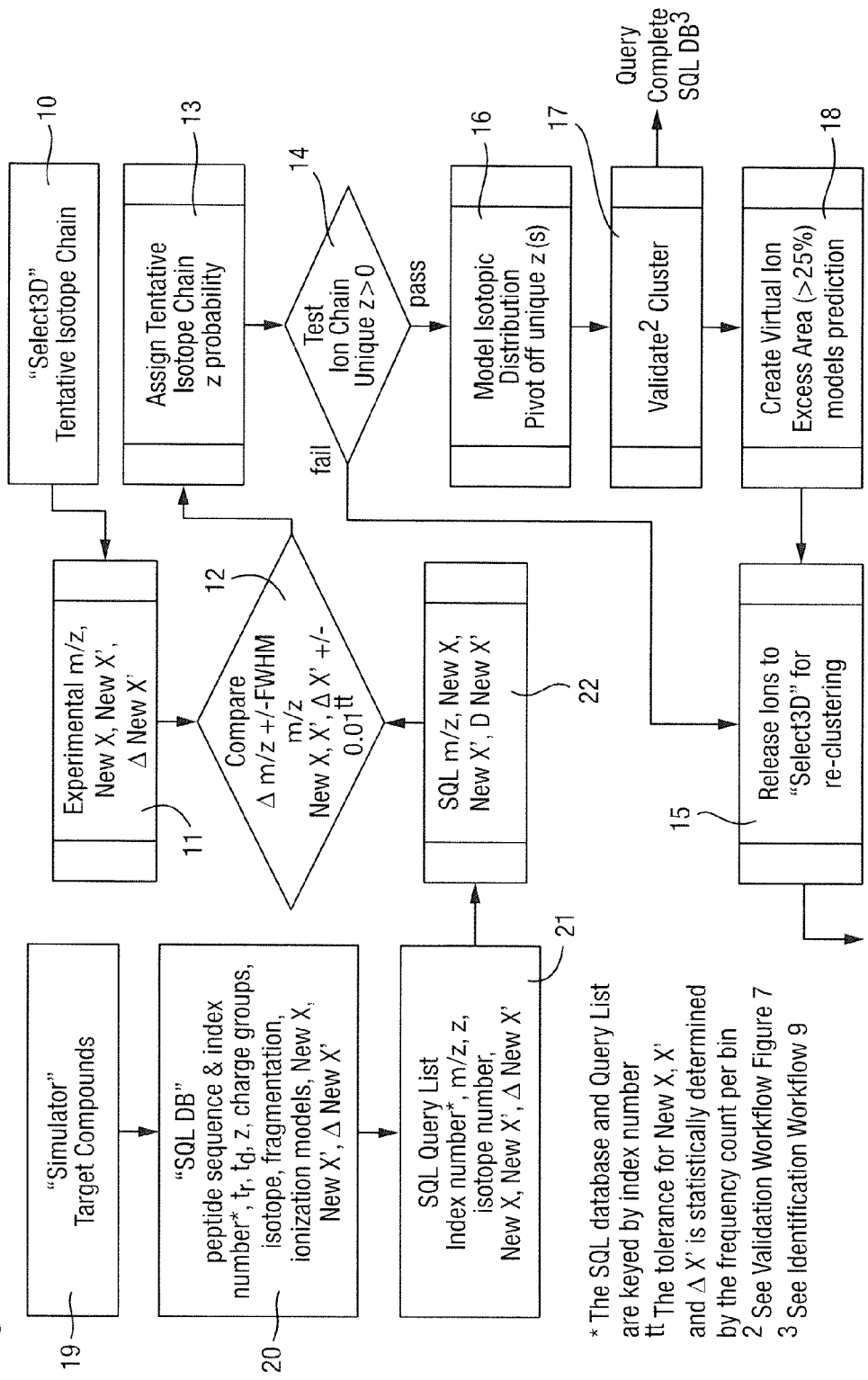

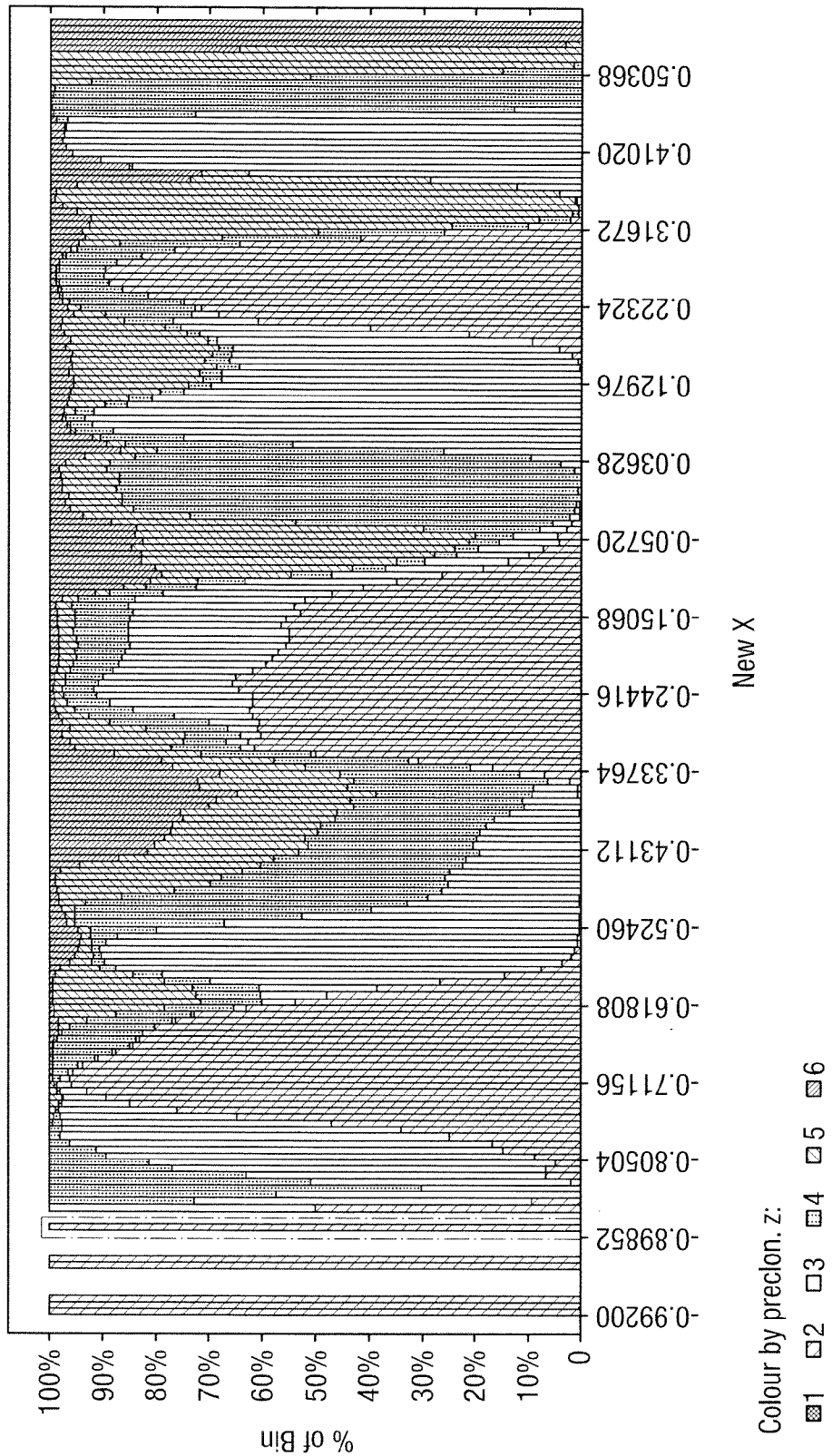

Complete Array (2000 Human Proteins, 1,264,212 isotopes, 5 charge-states)

Colour represents z length represents
% of all the ions illustrating that New X

Colour by preclon. z:
▨1 ☐2 ☐3 ▥4 ☐5 ▧6

Fig. 10A
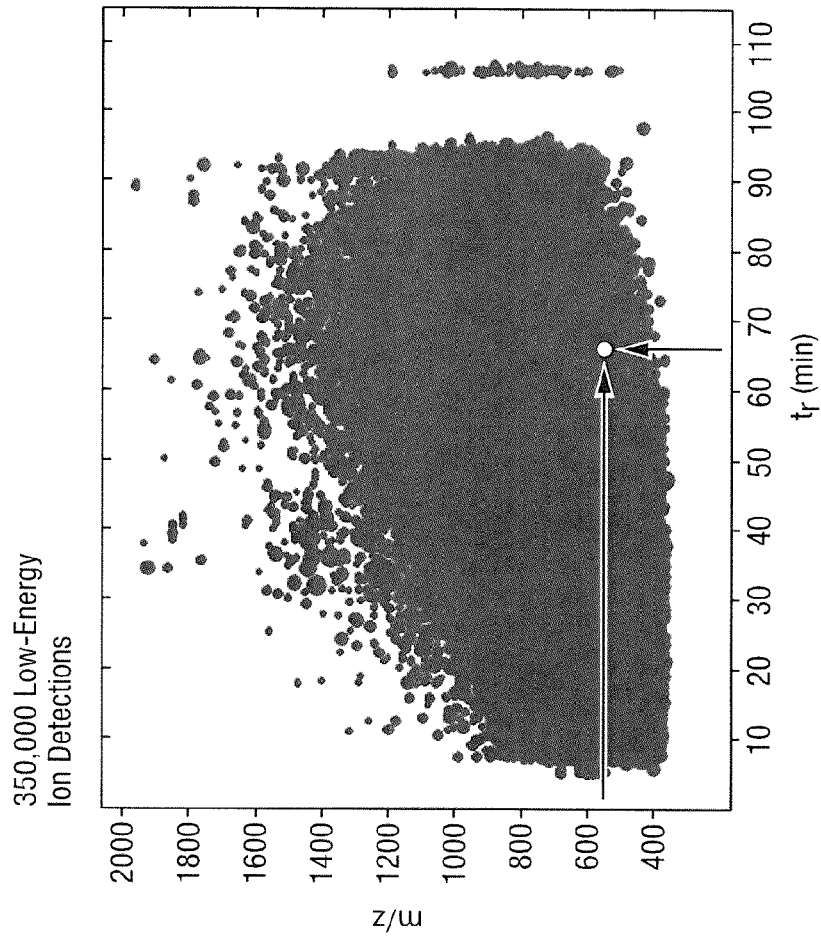
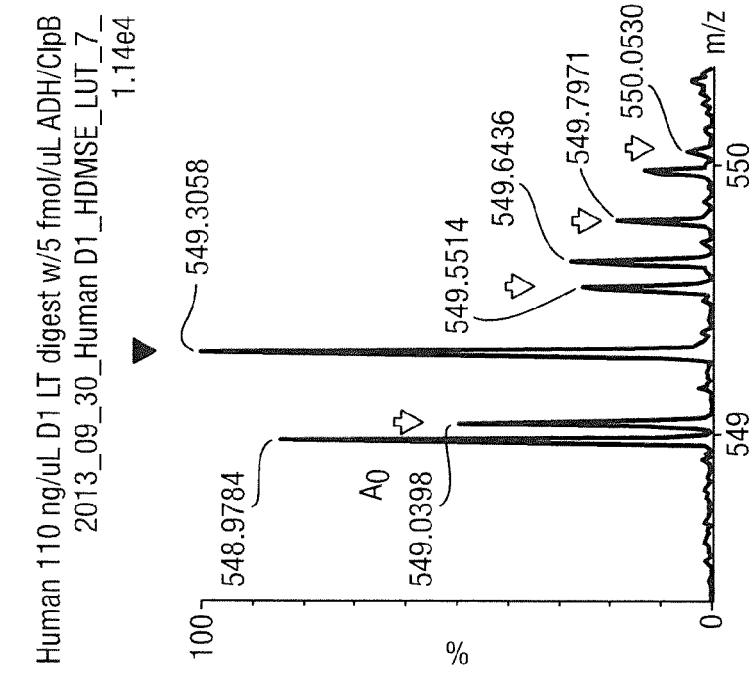

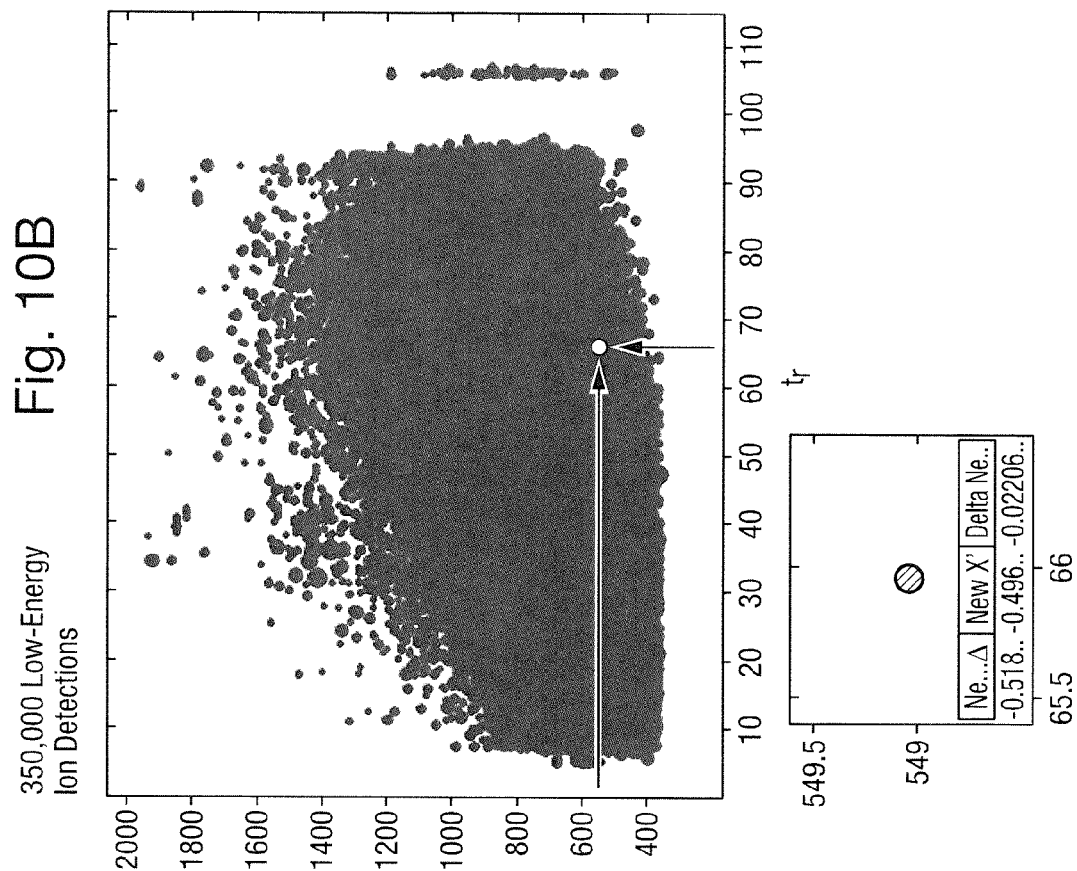
Fig. 10B
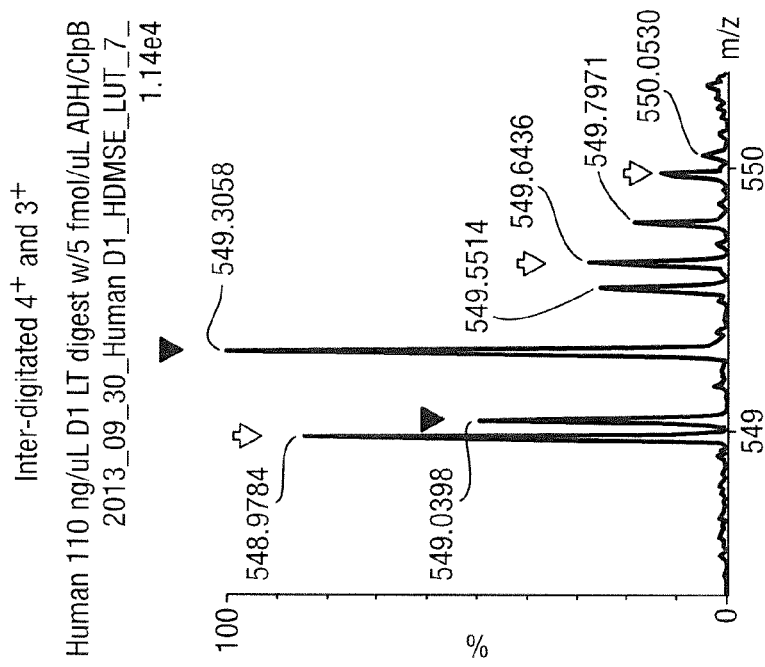

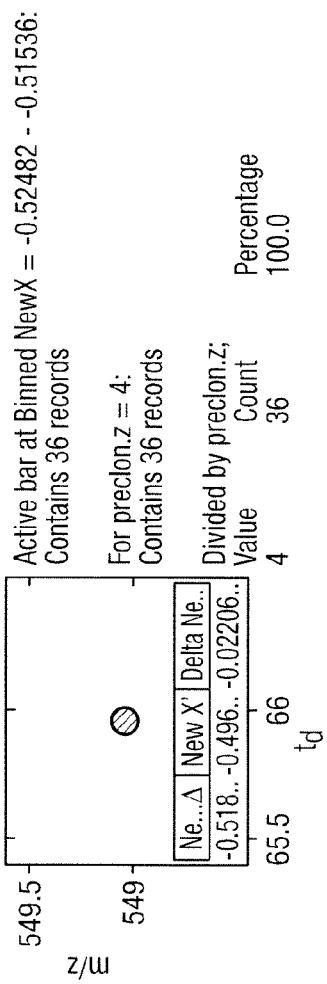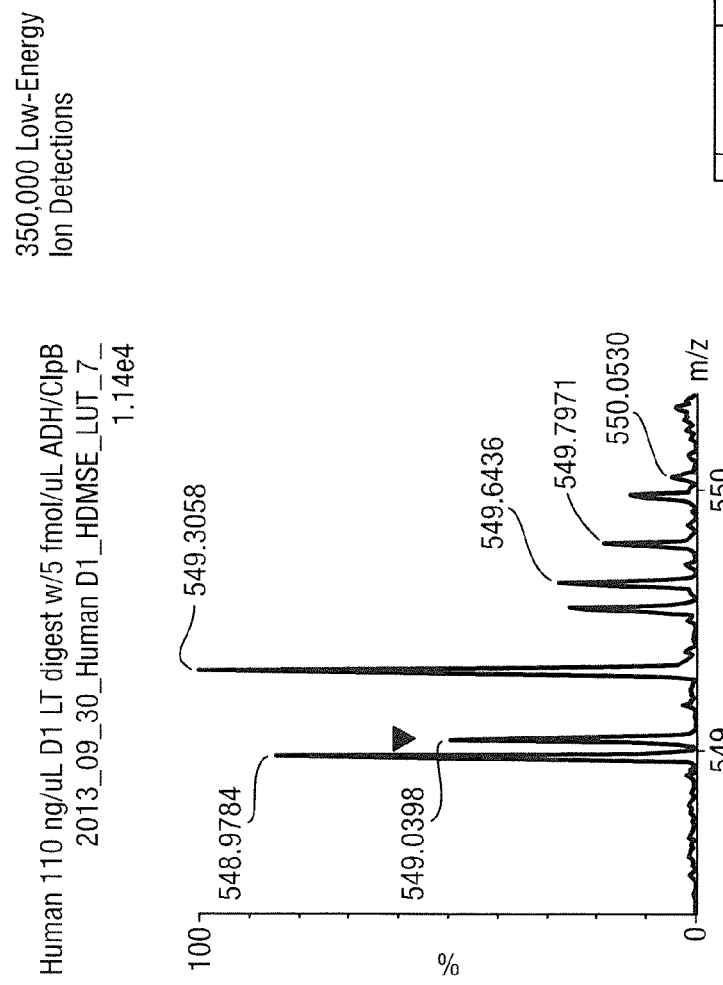
Fig. 10C

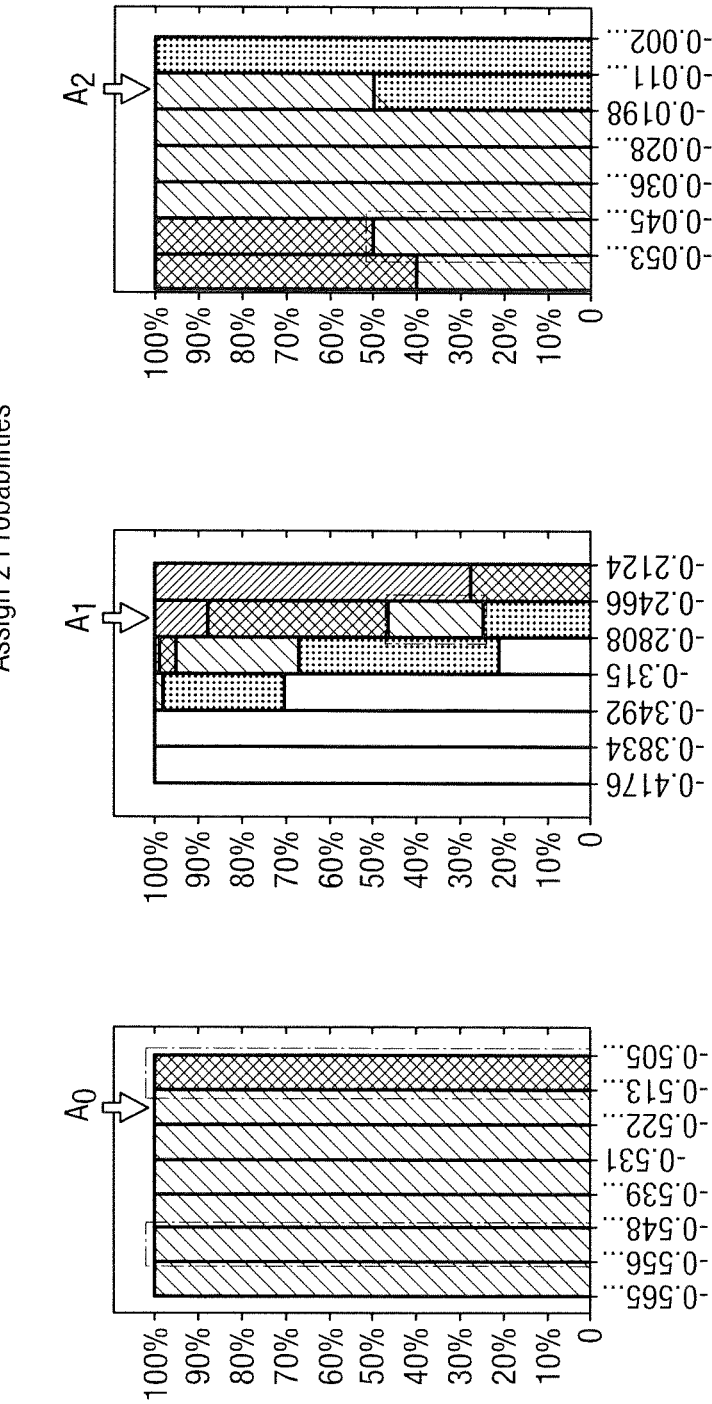
Fig. 13(Cont. I)

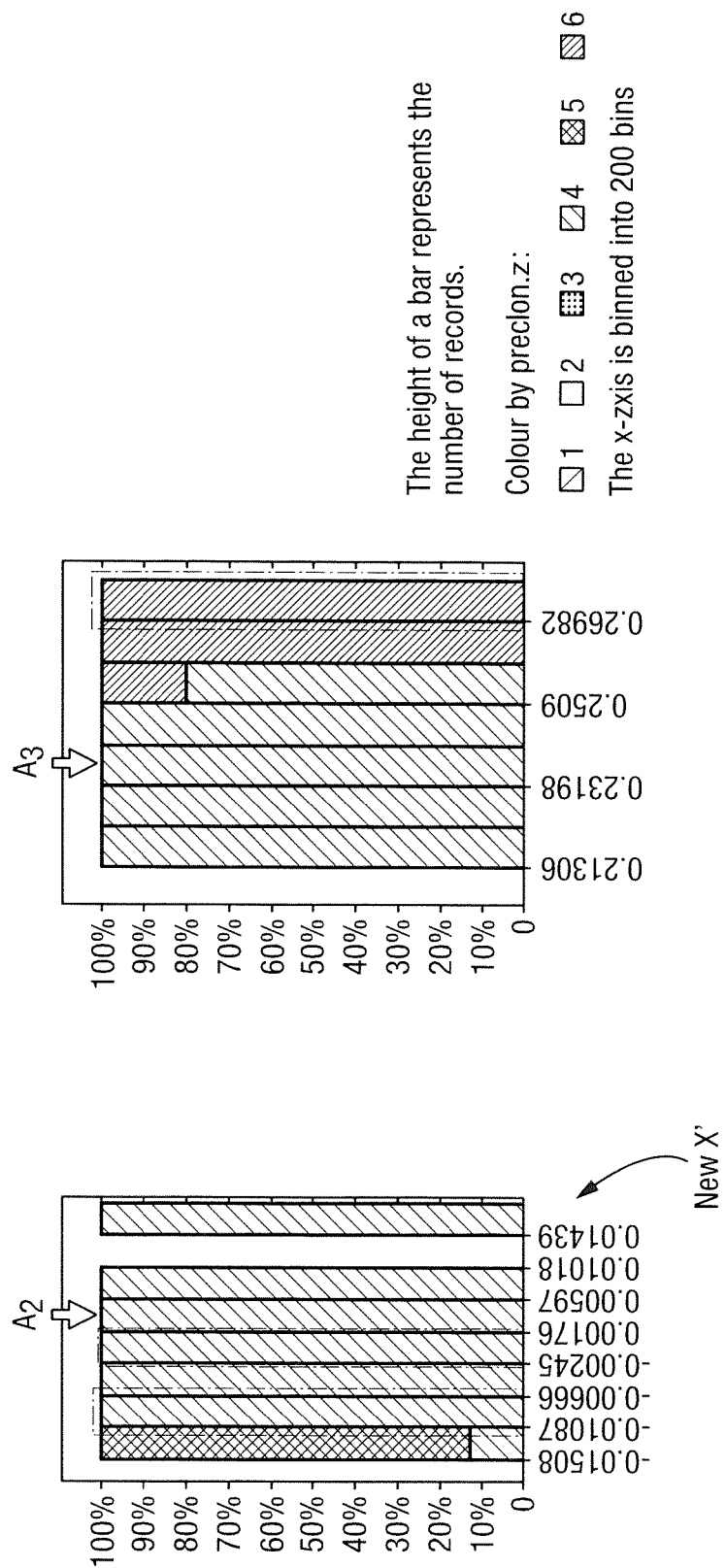

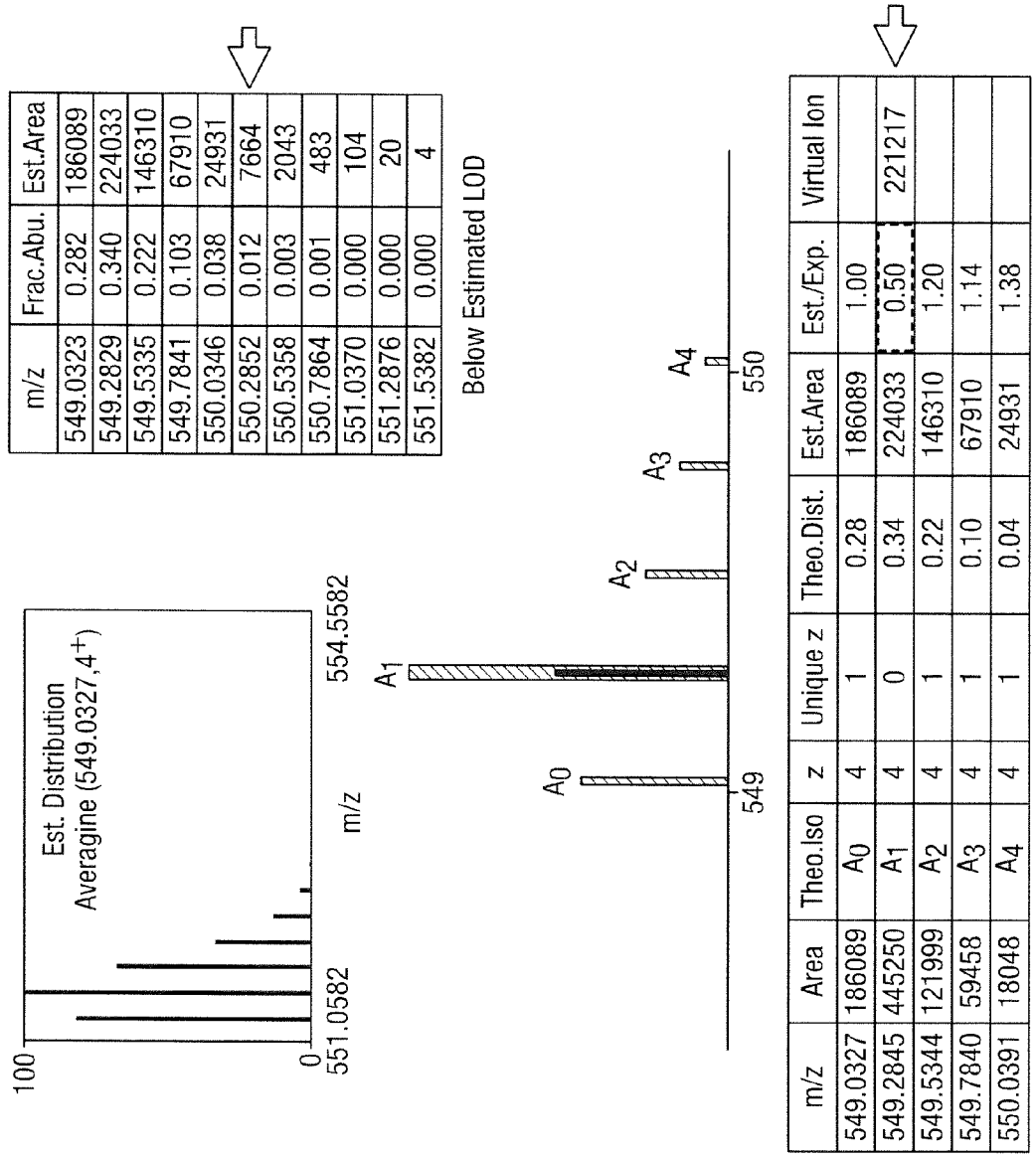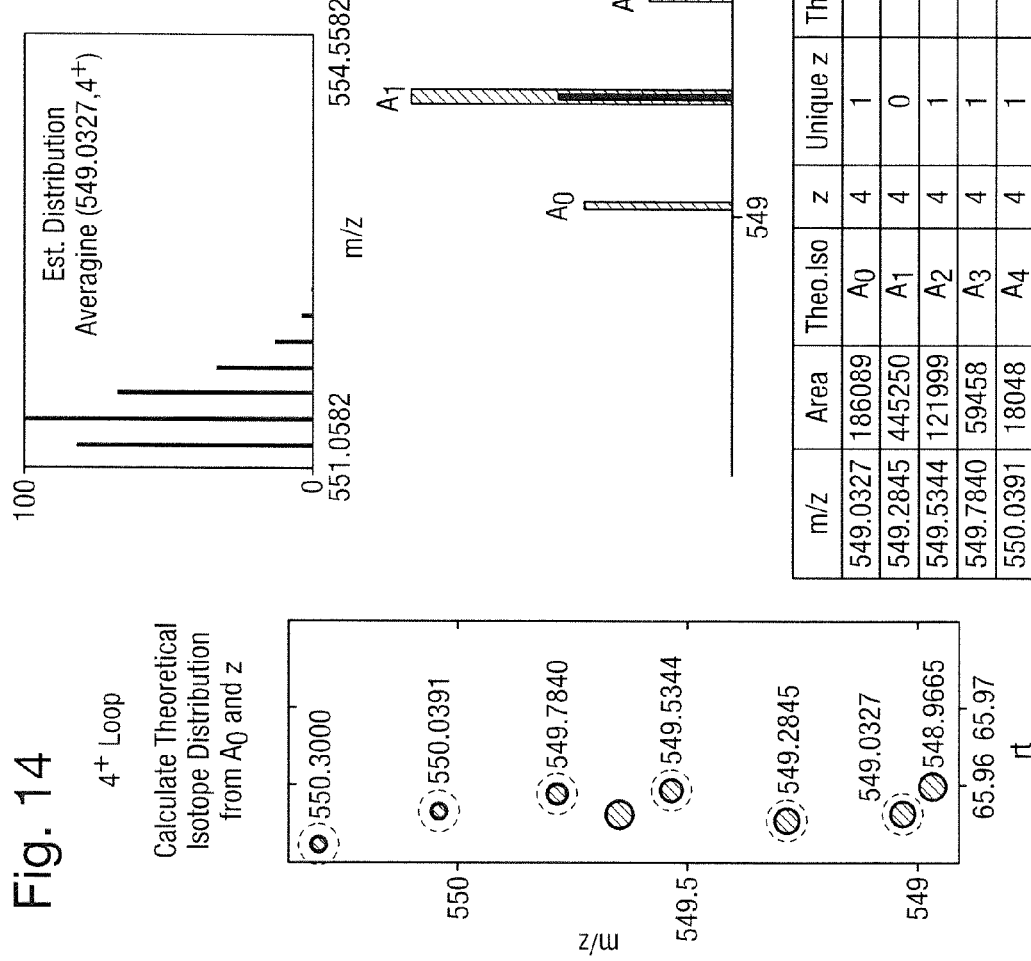
Fig. 14

An $A_0$, $3^+$ ion of m/z 729.3981 and 37,847 abitrary area counts should theorectically have 3 companion isotopes above the LOD. Clearly, what's illustrated is a series of inter-digitated $3^+$ charge clusters with a few $2^+$ to boot.

SYSTEM AND METHOD FOR ENHANCING CHARGE-STATE DETERMINATION IN ELECTROSPRAY MASS SPECTROMETRY

CROSS-REFERENCE TO RELATED APPLICATION APPLICATIONS

This application represents the U.S. National Phase of International Application number PCT/US2015/035540 entitled "System and Method for Enhancing Charge-State Determination in Electrospray Mass Spectrometry" filed 12 Jun. 2015, which claims priority from and the benefit of U.S. provisional patent application Ser. No. 62/011,665 filed on 13 Jun. 2014. The entire contents of these applications are incorporated herein by reference.

FIELD OF THE INVENTION

The present invention relates generally to a method of mass spectrometry and a mass spectrometer.

BACKGROUND

The accurate identification of product ion spectra (MS/MS) or precursor ion mass to charge ratio (mass fingerprinting) is predicated on the ability of a de-isotoping algorithm to correctly assign the charge state (z) of ions and determine the lowest mass peak $A_0$ of an isotopic distribution (also known as the monoisotopic mass).

Due to the lack of elemental variability in biomolecules (peptide, lipids, metabolites etc.) the process of seeking to determine the charge state of the ions and determine the lowest mass peak $A_0$ of an isotopic distribution can be particularly problematic when analysing either a simple or a complex biomolecule mixture since certain mass to charge ratio values can exist at multiple charge states.

Furthermore, there can be both inter-digitated and overlapping ion clusters which will cause significant problems for the de-isotoping algorithm to resolve.

It is desired to provide an improved method of mass spectrometry.

SUMMARY

According to an aspect there is provided a method of mass spectrometry comprising:
  ionising a sample and obtaining mass spectral data relating to a plurality of ion detection events;
  applying match tolerances for mass to charge ratio (m/z) and at least one of: chromatographic retention time ($t_r$); and ion mobility drift time ($t_d$), to the ion detection events in order to determine possible charge state connections;
  constructing a tentative isotope chain and querying ion detection events for a match to the tentative isotope chain;
  wherein once a tentative isotope chain has been constructed, the method further comprises:
  determining a corresponding theoretical molecular mass and a corresponding theoretical isotopic distribution;
  querying one or more lookup tables and returning one or more parameters (New X, New X', Δ New X') related to the fractional mass to charge ratio ($f_{m/z}$) and at least one of: ion mobility drift time ($t_d$); and nominal mass to charge ratio ($N_{m/z}$); of the ion detection events; and using the one or more parameters (New X, New X', Δ New X') to determine a unique charge state of the ions.

In embodiments, the method may further comprise analysing and processing a control sample prior to analysing the sample in order to validate instrument performance. The method may further comprise analysing and processing a control sample prior to analysing the sample in order to update a simulation model. The method may further comprise removing chemical noise from the mass spectral data.

In embodiments, the method may further comprise parsing the ion detection events into a first group comprising singly charged ions and a second group comprising multiply charged ions. The method may further comprise sorting the ion detection events in the second group by intensity or ion area. The method may further comprise sorting the ion detection events in descending order of intensity or ion area up to a user or algorithmically derived maximum ion count. The method may further comprise removing ion detection events exceeding the maximum ion count. The method may further comprise sorting the selected ion detection events by mass to charge ratio in ascending order.

In embodiments, the step of applying a tolerance for chromatographic retention time ($t_r$) may comprise setting a tolerance at a fraction or percentage of the chromatographic retention time at the full width half maximum of a retention time peak. The step of applying a tolerance for mass to charge ratio may comprise setting a tolerance at a fraction or percentage of the mass to charge ratio at the full width half maximum of a mass to charge ratio peak. The step of applying a tolerance for ion mobility drift time may comprise setting a tolerance at a fraction or percentage of the ion mobility drift time at the full width half maximum of an ion mobility peak. A possible charge state connection may be confirmed if a companion ion is located having a mass to charge ratio and/or chromatographic retention time and/or ion mobility drift time within the tolerances.

In embodiments, the step of constructing a tentative isotope chain may further comprise initially selecting an ion detection event having the lowest mass to charge ratio and the highest charge state. The method may further comprise querying remaining ion detection events for a match within a mass to charge ratio tolerance. If a tentative isotope chain cannot be constructed then an ion having the next highest mass to charge ratio may be selected and remaining ion detection events may then be queried for a match within a mass to charge ratio tolerance.

In embodiments, once a tentative isotope chain has been constructed then the first ion in the isotope chain and having a charge state z may be assumed to correspond with an $A_0$ ion. The step of determining a corresponding theoretical molecular mass and a corresponding theoretical isotopic distribution may be made on the basis of the charge state z and the mass to charge ratio of the $A_0$ ion.

In embodiments, the method may further comprise comparing the number of ions (L) in a tentative isotope chain to a predicted number of ions. If the number of ions (L) in the tentative isotope chain is determined to be greater than or equal to the predicted number of ions then the tentative isotope chain may be allowed to proceed for further processing. If the number of ions (L) in the tentative isotope chain is determined to be less than the predicted number of ions then the tentative isotope chain may be no longer considered as representing a tentative isotope chain.

In embodiments, the step of querying the lookup table may further comprise limiting the mass to charge ratio range to the full width half maximum of a mass to charge ratio peak.

In embodiments, the method may further comprise transforming the fractional mass to charge ratio ($f_{m/z}$) and ion mobility drift time ($t_d$) of ion detection events to determine a first parameter (New X). The method may further comprise transforming the fractional mass to charge ratio ($f_{m/z}$) and nominal mass to charge ratio ($N_{m/z}$) of ion detection events to determine a second parameter (New X'). The method may further comprise determining the difference (Δ New X') between the second parameter (New X') and the first parameter (New X). The one or more parameters may be calculated on-the-fly and/or may be calculated during the generation of the one or more lookup tables.

In embodiments, the one or more lookup tables may be derived from a database of bio-molecules or molecules of biological origin. The database may comprise simulated proteomes, metabolomes or lipidomes.

In embodiments, the method may further comprise distributing the one or more parameters amongst a plurality of mass or mass to charge ratio bins. The method may comprise setting the width of the mass or mass to charge ratio bins based upon a minimum number of representation ions for calculating charge state probabilities. The method may comprise calculating a distribution of charge states and determining the probability of each possible charge state.

In embodiments, if the use of one of the parameters is insufficient to determine a unique charge state of the ions then the method may further comprise using another of the parameters to determine a unique charge state of the ions. If a unique charge state for the ions cannot be determined then the tentative isotope chain may be no longer considered to represent a tentative isotope chain.

Once a unique charge state of the ions has been determined the method may further comprise estimating a summed area for the complete isotope chain. The step of estimating the summed area for the complete isotope chain comprises dividing the area of the lowest mass to charge ratio ion having a unique charge state by its theoretical abundance. If the ratio of a theoretical ion area to the area of an ion detection event is within a desired tolerance then the tentative isotope chain may be considered to comprise a valid isotope cluster. If the ratio of a theoretical ion area to the area of an ion detection event is <1 then the method may further comprise creating a virtual ion. If the ratio of a theoretical ion area to the area of an ion detection event is >1 then the method may further comprise recalculating the summed area.

The method according to an embodiment provides the ability to correctly de-isotope, de-convolve and distribute (segment) the area of overlapping, inter-digitated and/or composite ion spectra. The method according to an embodiment represents a significant advance in the art in achieving both clarity (correct determination of mass to charge ratio) and depth-of-coverage across the entire experimental dynamic range.

With respect to accurate quantification, the ability to correctly parse the area of two ions having similar mass to charge ratios but different charge states or isotope number is important to providing precise area counts for accurate quantification.

Conventional methods of ion detection (in contrast to embodiments) do not accurately determine either on-the-fly or post-acquisition a unique charge state or possible charge states of a single ion.

For ions with a measured mass to charge ratio capable of existing at multiple charge states each charge state may be annotated with its probability.

In targeted analyses the ability to correctly predict the charge state z of an ion limits precursor ion selection to only those isotopes having a unique charge state z. This ability maximizes both the duty-cycle and selectivity of the employed workflow.

According to another aspect there is provided a mass spectrometer comprising:
an ion source for ionising a sample;
an ion detector system for obtaining mass spectral data relating to a plurality of ion detection events; and
a control system arranged and adapted:
(i) to apply match tolerances for mass to charge ratio (m/z) and at least one of: chromatographic retention time ($t_r$); and ion mobility drift time ($t_d$) to said ion detection events in order to determine possible charge state connections;
(ii) to construct a tentative isotope chain and to query ion detection events for a match to said tentative isotope chain;
wherein once a tentative isotope chain has been constructed, said control system is further arranged and adapted:
(iii) to determine a corresponding theoretical molecular mass and a corresponding theoretical isotopic distribution;
(iv) to query one or more lookup tables and to return one or more parameters (New X, New X', Δ New X') related to the fractional mass to charge ratio ($f_{m/z}$) and at least one of: ion mobility drift time ($t_d$); and nominal mass to charge ratio ($N_{m/z}$) of said ion detection events; and
(v) to use said one or more parameters (New X, New X', Δ New X') to determine a unique charge state of said ions.

According to another aspect there is provided a method of mass spectrometry comprising:
ionising a sample and obtaining mass spectral data relating to a plurality of ion detection events;
applying match tolerances for chromatographic retention time ($t_r$), mass to charge ratio (m/z) and optionally ion mobility drift time ($t_d$) to said ion detection events in order to determine possible charge state connections;
constructing a tentative isotope chain and querying ion detection events for a match to said tentative isotope chain;
wherein once a tentative isotope chain has been constructed, said method further comprises:
determining a corresponding theoretical molecular mass and a corresponding theoretical isotopic distribution;
querying one or more lookup tables and returning one or more parameters (New X, New X', Δ New X') related to the fractional mass to charge ($f_{m/z}$) and/or ion mobility drift time ($t_d$) and/or nominal mass to charge ratio ($N_{m/z}$) of said ion detection events; and
using said one or more parameters (New X, New X', Δ New X') to determine a unique charge state of said ions.

According to another aspect there is provided a mass spectrometer comprising:
an ion source for ionising a sample;
an ion detector system for obtaining mass spectral data relating to a plurality of ion detection events; and
a control system arranged and adapted:
(i) to apply match tolerances for chromatographic retention time ($t_r$), mass to charge ratio (m/z) and optionally ion mobility drift time ($t_d$) to said ion detection events in order to determine possible charge state connections;
(ii) to construct a tentative isotope chain and to query ion detection events for a match to said tentative isotope chain;

wherein once a tentative isotope chain has been constructed, said control system is further arranged and adapted:

(iii) to determine a corresponding theoretical molecular mass and a corresponding theoretical isotopic distribution;

(iv) to query one or more lookup tables and to return one or more parameters (New X, New X', Δ New X') related to the fractional mass to charge ($f_{m/z}$) and/or ion mobility drift time ($t_d$) and/or nominal mass to charge ratio ($N_{m/z}$) of said ion detection events; and (v) to use said one or more parameters (New X, New X', Δ New X') to determine a unique charge state of said ions.

According to another aspect there is provided a method of mass spectrometry comprising:

ionising a sample and obtaining mass spectral data relating to a plurality of ion detection events;

applying match tolerances for chromatographic retention time ($t_r$), mass to charge ratio (m/z) and optionally ion mobility drift time ($t_d$) to the ion detection events in order to query the complete plurality of ion detections for charge state or z-connections, wherein a charge state or z-connection relates to a matched ion from the plurality of ion detections whose m/z is optionally equal to the queried m/z +/−1/z wherein z optionally goes from highest-to-lowest, within the applied m/z, $t_r$ and if employed $t_d$ match tolerances;

calculating a fractional m/z of each ion detection from the plurality of ion detections optionally by subtracting the integer m/z value of each m/z from its m/z, transforming the fractional m/z versus $t_d$, or in the absence of ion mobility, transforming the fractional m/z versus nominal m/z in order to calculate a transformed value of New X or New X' respectively;

applying match tolerances for chromatographic retention time ($t_r$), mass to charge ratio (m/z) and optionally ion mobility drift time ($t_d$) to the ion detection events in order to construct tentative ion chains starting from the highest charge state z to the lowest;

applying match tolerances for comparing the experimentally derived New X and/or New X' values to a series of lookup tables of calculated New X, New X' to determine a unique charge state of the ions;

wherein the unique status of each ions' charge-state is validated by comparison to its charge state or z-connections, wherein an ions charge-state can be adjusted if it has a unique charge state z-connection but multiple charge state or z values from comparison(s) of New X and/or New X';

wherein optionally if an ion has multiple charge state or z-connections but only a single charge state z from comparison of New X and/or New X' then the method further comprises revoking the unique charge state or z status;

wherein once a tentative isotope chain has been constructed, the method further comprises:

determining a corresponding theoretical molecular mass and a corresponding theoretical isotopic distribution;

optionally determining an estimated sum ion cluster intensity utilizing the experimental ion areas of the unique charge state or z ions in the chain;

optionally calculating a theoretical ion area for each ion in the tentative ion cluster by multiplying the estimated sum ion cluster area by a theoretical fractional abundance ratio of a theoretical model by isotope number;

optionally calculating a best fit of the clustered data to the theoretical model by taking the ratio of the experimental ion area to the calculated theoretical area determined by multiplying the estimated sum ion cluster area by the theoretical fractional abundance ratio of the theoretical model by isotope number;

optionally determining composite ion clusters by their area ratios and optionally creating virtual ions by keeping all the physico-chemical attributes of the composite ion excluding the experimental ion area replacing the experimental ion area with the difference between the experimental ion area and its theoretical ion area;

wherein optionally for ions contained in an ion cluster that are in saturation where the experimental ion area is compromised, the compromised area is replaced with the theoretical ion area generated from the estimated sum ion cluster area.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage may have an amplitude selected from the group consisting of: (i) < about 50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) > about 500 V peak to peak.

The AC or RF voltage may have a frequency selected from the group consisting of: (i) < about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) > about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) < about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) > about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which:

FIG. 2 shows how ion detections are divided into singly charged and multiply charged groups and tentative isotope chains are constructed for each group;

FIG. 4A shows singly charged ions being group together in a first bin and FIG. 4B shows multiple charged ions being placed in a second bin;

FIG. 6 shows the steps involved in comparing tentative charge groups (isotope clusters);

FIG. 10A illustrates how embodiments may seek to resolve inter-digitated $4^+$ and $3^+$ ion detections present in a complex sample comprising 350,000 low energy ion detections, FIG. 10B shows the process of creating a phantom $3^+$ cluster and FIG. 10C shows in more detail the process of the determining the charge state of an ion having a mass to charge ratio of 549.0398 as being $4^+$;

FIG. 14 shows a $4^+$ loop and illustrates the step of creating a virtual ion;

DETAILED DESCRIPTION

An embodiment will now be described.

The lack of elemental (C,N,H,O,S,P) variability in the construction of bio-molecules gives rise to the problem of there being overlapping and/or inter-digitated (chimeric) ion clusters within the mass to charge ratio range of a predicted isotopic distribution. The frequency of chimeric interaction is proportional to mass to charge ratio, elution position and sample, type (Stable Isotope Labelling) and complexity.

An embodiment seeks to improve the determination of the charge state of ions from a mass spectrum.

Figure 1:
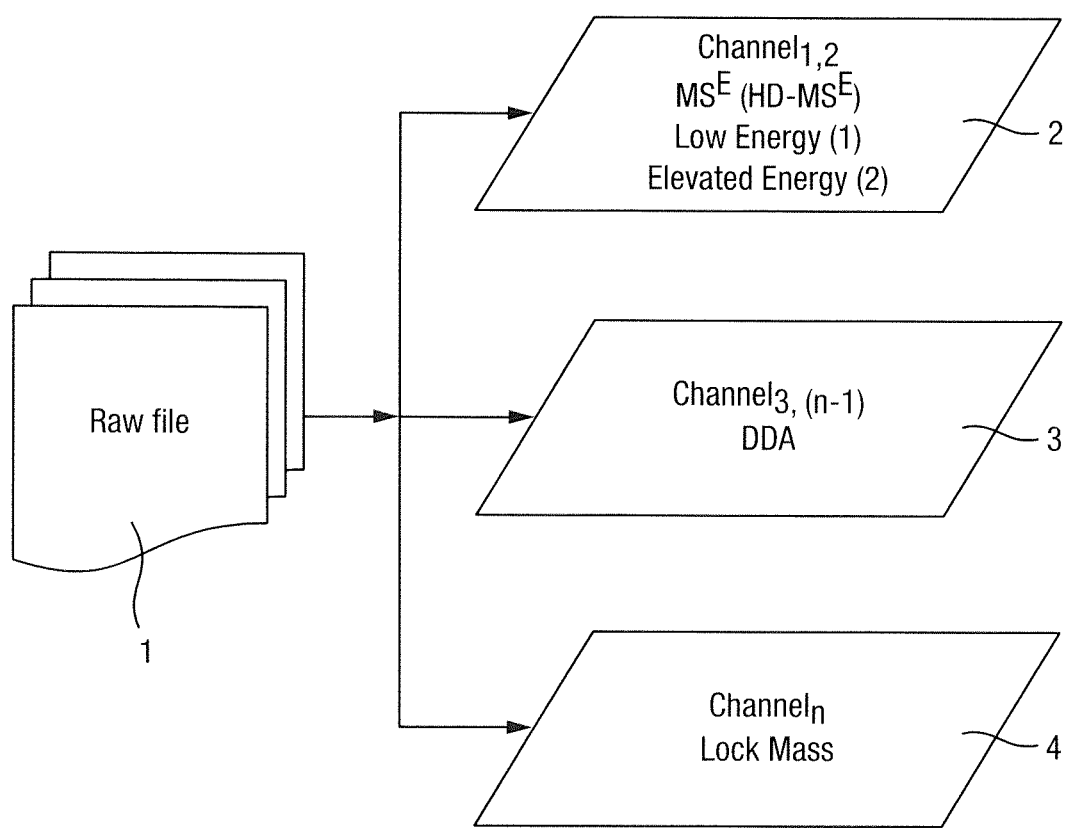
FIG. 1 shows a raw data file comprising a plurality of data channels including MSE data acquired at low energy and elevated energy (channels #1 and #2), DDA data (channel #3 through to channel #n−1) and lock mass data (channel #n)

FIG. 1 illustrates a raw data file 1 which according to an embodiment comprises a plurality of channels including $MS^E$ data 2 acquired at low energy (channel #1) and at elevated energy (channel #2), Data Dependent Acquisition ("DDA") data 3 (channels #3 to channel #n−1) and lock mass data 4 (channel #n).

FIG. 2 shows how ion detections may be divided into singly charged and multiply charged groups.

If the mass to charge (m/z) of ions is plotted as a function of the ion mobility drift time ($t_d$) of the ions, then ions having a value of m/z $t_d$<8.8 are determined as corresponding to singly charged ions whereas ions having a m/z/$t_d$>8.8 are determined as corresponding to multiply charged ions.

For the singly charged ions a tentative isotope chain may be constructed starting from the lowest mass to charge ratio ion to the highest mass to charge ratio ion with a tolerance of Δm/z=1, $\Delta t_r$=0.2×FWHM and $\Delta t_d$=FWHM.

For the multiply charged ions a tentative isotope chain is constructed from lowest mass to charge ratio ion to the highest mass to charge ratio and starting from the maximum charge state z first down to lowest charge state z=2, with tolerances set at Δm/z=1/z, $\Delta t_r$ being a user-defined or algorithmically derived percentage of the FWHM and $\Delta t_d$=FWHM.

Tentative isotope chains are then compared with simulated data.

Figure 3A:
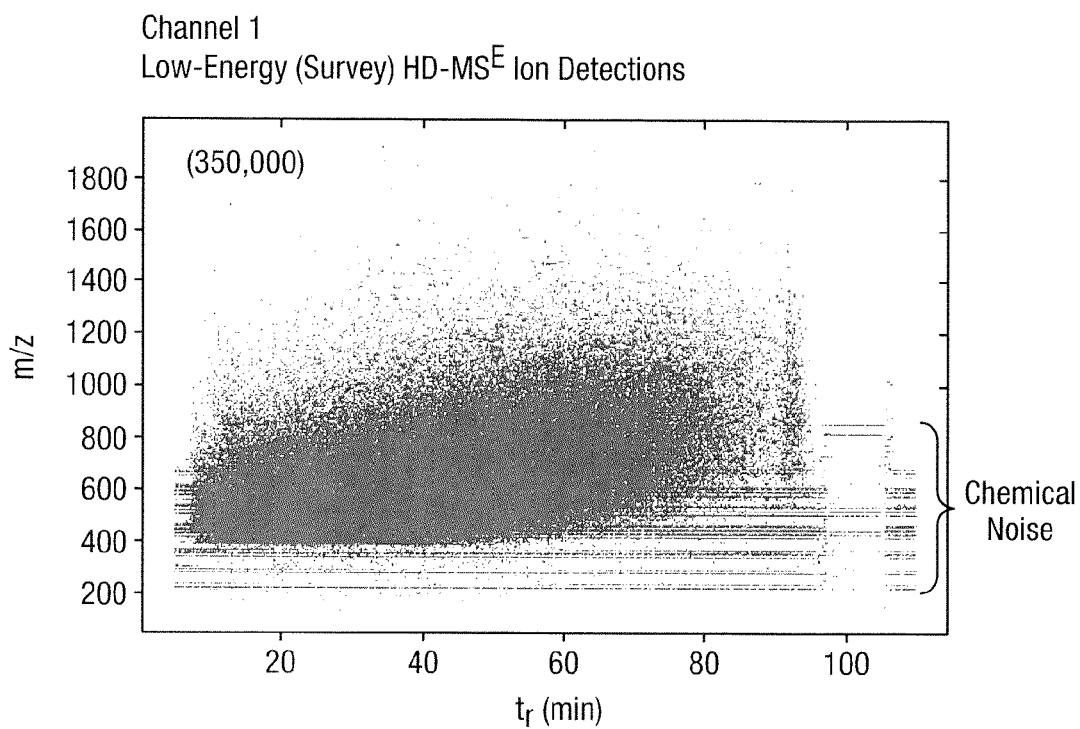
FIG. 3A shows a plot of mass to charge ratio versus chromatographic retention time which includes chemical noise.
Figure 3B:
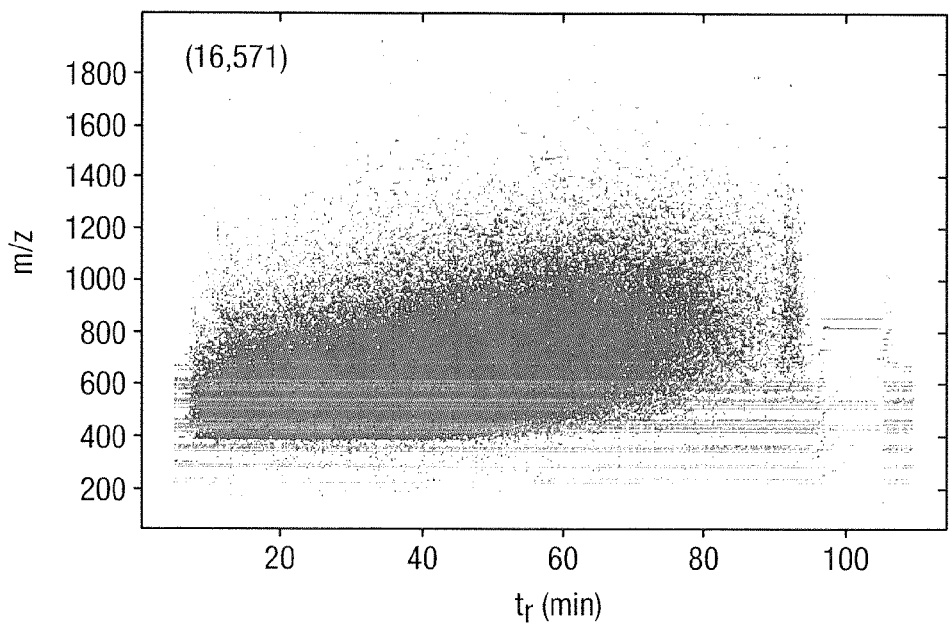
FIG. 3B illustrates the removal of background chemical noise.

FIG. 3A shows mass spectral data from channel #1 (low energy survey mass spectral data) and shows approximately 350,000 ion arrival events having been detected. Chemical noise may be removed as shown in FIG. 3B. Chemical noise is apparent in FIGS. 3A and 3B as a series of horizontal lines in the plots of mass to charge ratio (m/z) against chromatographic retention time ($t_r$).

Figure 3C:
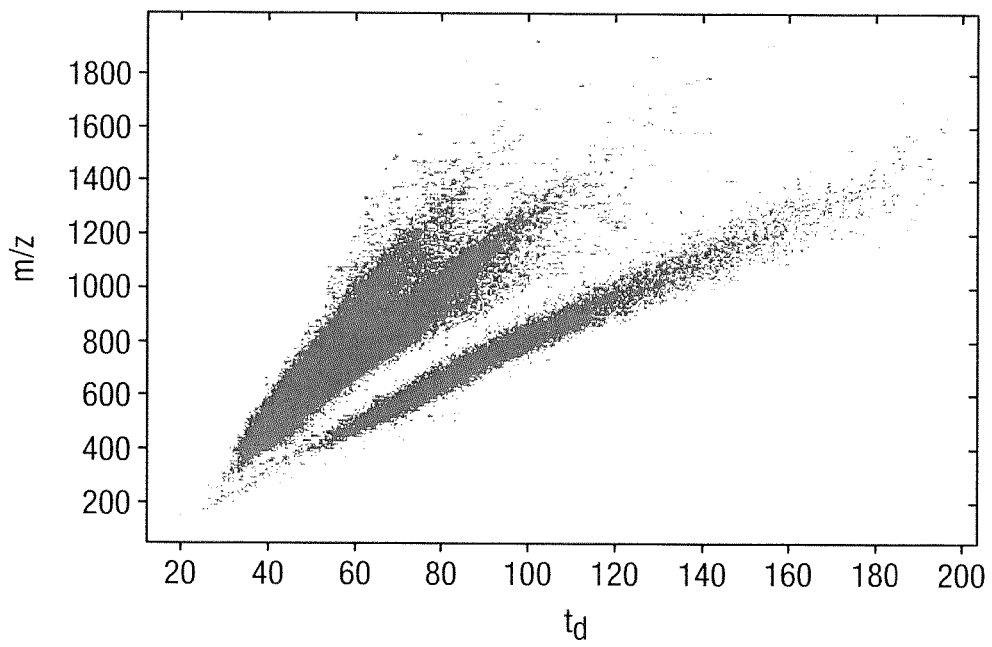
FIG. 3C shows a plot of mass to charge ratio versus ion mobility drift time.
Figure 3D:
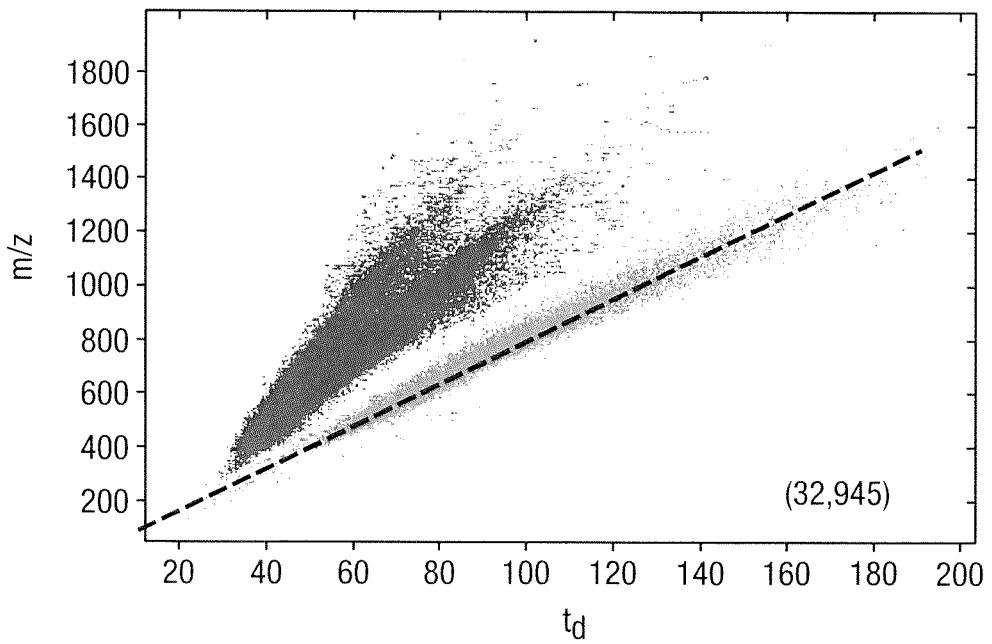
FIG. 3D shows a plot of mass to charge ratio versus ion mobility drift time and highlights singly charged ions resulting from in-source fragmentation.
Figure 3E:
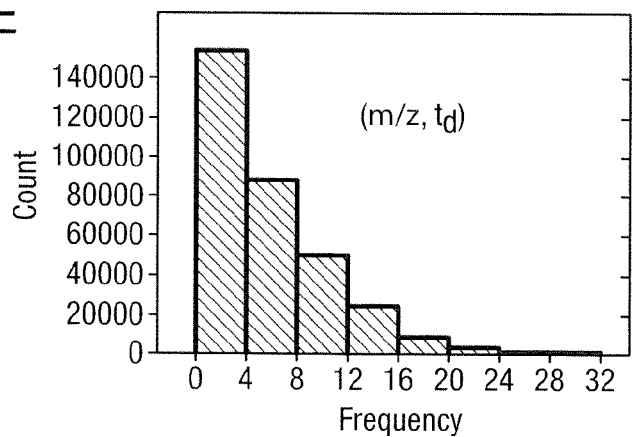
FIG. 3E shows a histogram of ion count for ions having a particular mass to charge ratio and ion mobility drift time.
Figure 3F:
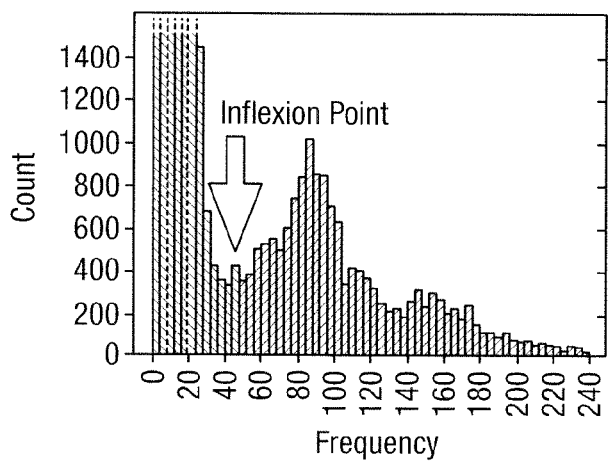
FIG. 3F illustrates how an inflexion point may be used to remove chemical noise and FIG. 3G further illustrates how ions may be divided into a first group comprising singly charged ions and a second group comprising multiply charged ions.

A histogram of the count of ions having a particular mass to charge ratio and ion mobility drift time $t_d$ may be generated as shown in FIG. 3E. FIG. 3E shows how the ion count exceeds 140,000 for the low frequency bins. FIG. 3F shows the same data but up to a frequency of 240 and wherein the actual ion count at low frequencies exceeds the displayed maximum ion count which is shown of 1400.

In FIG. 3E the frequency is only shown up to 32 and the ion detections are all considered as relating to an analyte ion signal rather than chemical noise. In FIG. 3F the frequency is shown up to 240 and the ion count is only shown up to 1400. It will be understood that the maximum ion count at low frequencies is >20000 as shown in FIG. 3E.

A point of inflexion as shown in FIG. 3F is determined around a frequency of 48. Ions or mass spectral data in the histogram having a frequency ≤48 (the inflexion point) are determined to relate to ion signal whereas ions or mass spectral data having a frequency >48 (the inflexion point) are determined as relating to chemical noise.

Figure 16:
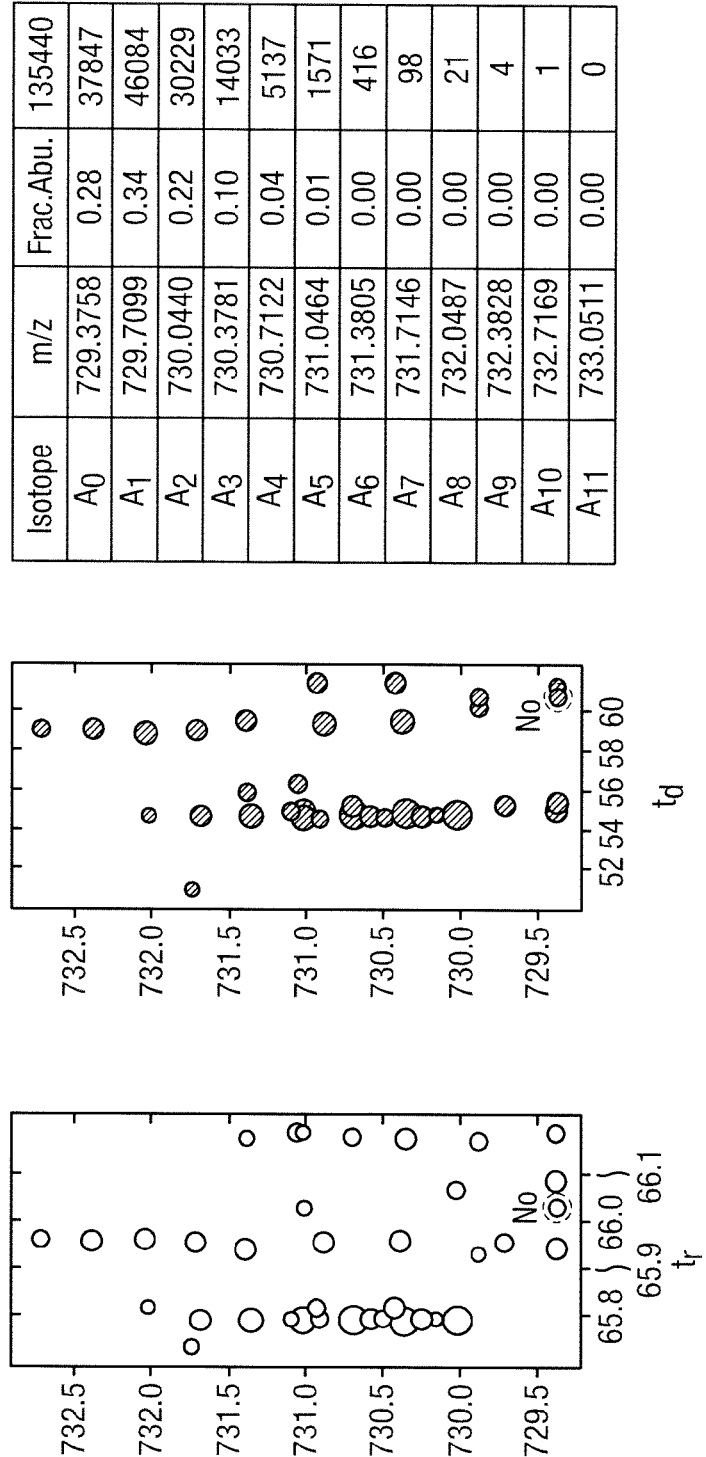
FIG. 16 illustrates the problem of determining where clusters start and end.
Figure 16:
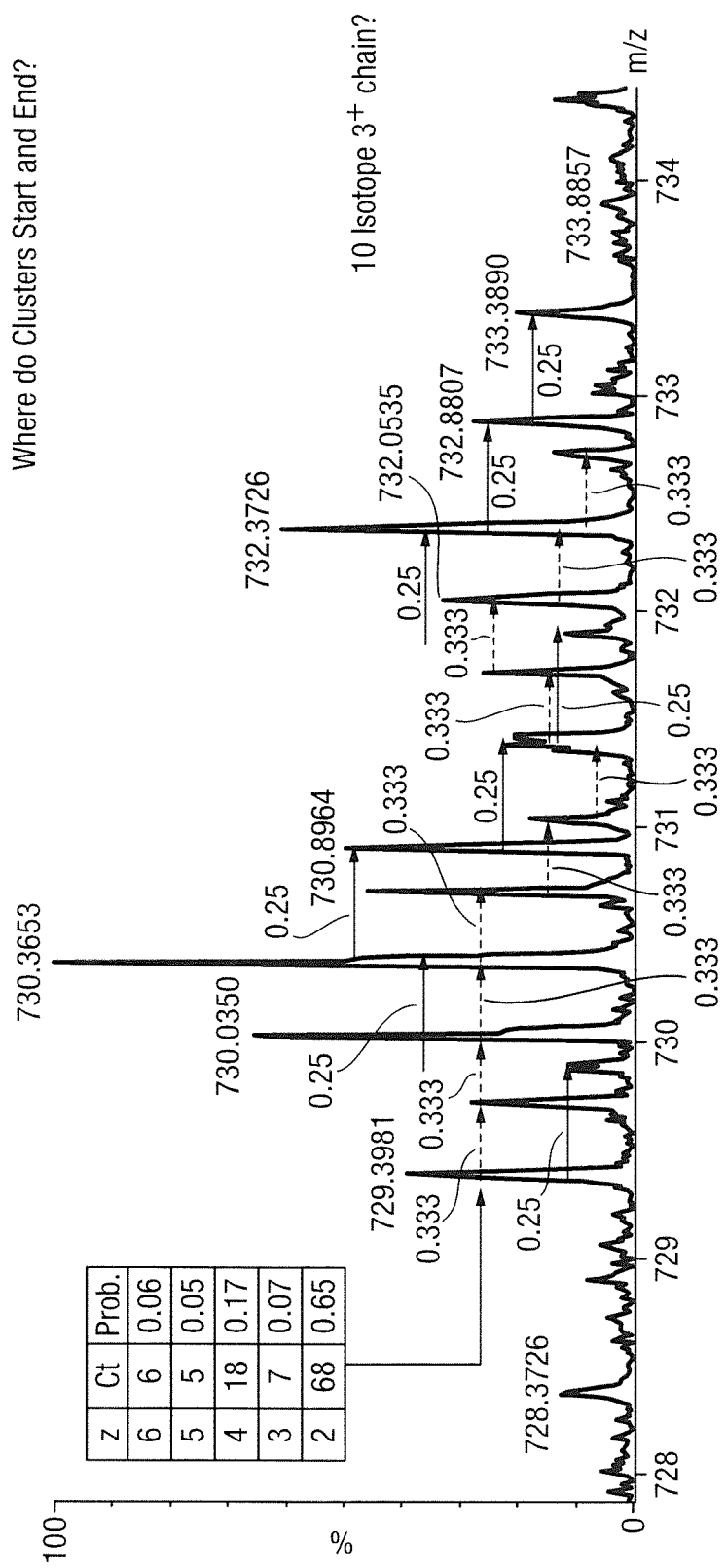

Ion detections which are determined as relating to chemical noise may be deleted or otherwise removed from the mass spectral data. With reference to the mass spectral data as shown in FIG. 3B, 16,571 ion arrival events are determined as relating to chemical noise and are duly removed from the mass spectral data.

FIGS. 3C and 3D shows plots of mass to charge ratio versus ion mobility drift time. Ions are shown in two distinct clusters. The first cluster relates to multiply charged ions and the second cluster relates to singly charged ions. The singly charged ions correspond with in source fragment ions which are useful for isobaric labelling. In the particular mass spectral data shown in FIG. 3D, 32,945 ion detections are determined as relating to singly charged ions.

Figure 3G:
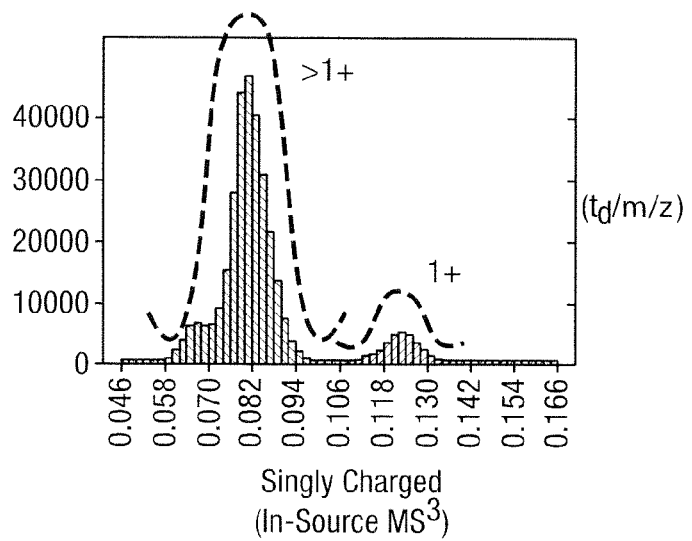

FIG. 3G shows a plot of $t_d$/m/z and shows how singly charged ions may be differentiated from multiply charged ions.

Once the ions have been filtered of chemical noise the raw ion detections are then parsed into two groups $1^+$ and $>1^+$ as illustrated in FIG. 2.

The charge state of an ion may be inferred by transforming the fractional mass to charge ratio and ion mobility drift time $t_d$ to a new value (New X). Alternatively, in the absence of ion mobility spectrometry ("IMS") data, the algorithm according to an embodiment may transform the integer or nominal mass to charge ratio versus the fractional mass to charge ratio to a new value (New X').

The selectivity of New X' relative to New X though not as great can be improved by utilizing additional relationships between chromatographic retention time $t_r$, ion mobility drift time $t_d$ and New X'.

An illustration of the transformations which may be applied are shown in FIGS. 4A, 4B, 5A, 5B and 5C and will be discussed in more detail below.

FIG. 4A shows low energy (i.e. survey scan) ion detections and highlights singly charged ions which have been recognised and which are treated separately. The singly charged ions result from in-source fragmentation.

FIG. 4B shows corresponding multiple charged ions which are placed in a separate bin for separate processing.

Figure 5A:
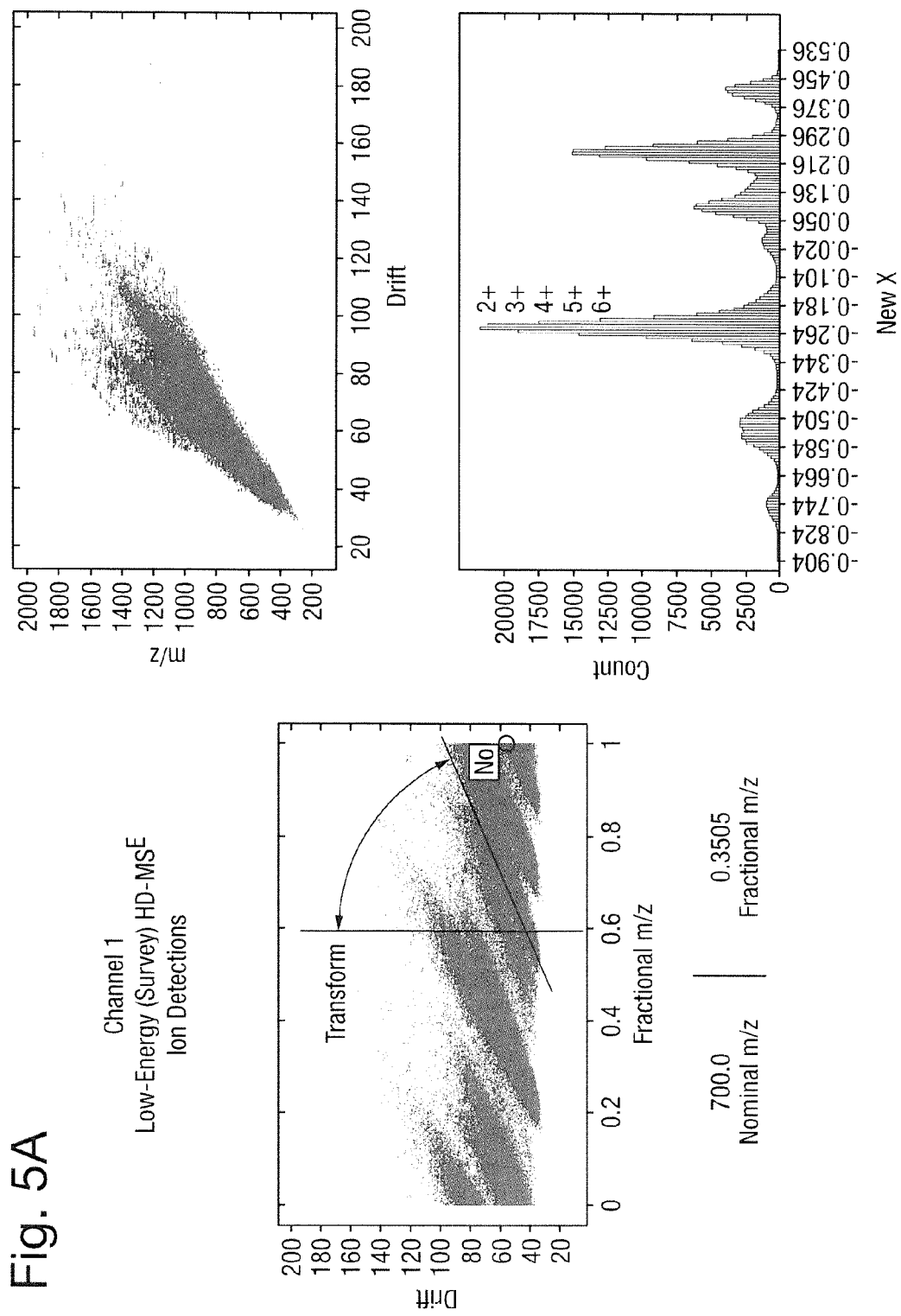
FIG. 5A shows a transformation that is applied to low-energy (survey) MSE ion detections to determine a value of New X.

FIG. 5A shows a plot of ion mobility drift time as a function of fractional mass to charge ratio. By way of example, it will be understood that ions having a mass charge ratio of, for example, 700.3505 may be considered as having an integer or nominal mass to charge ratio ($N_{m/z}$) of 700 and a fractional ($f_{m/z}$) mass to charge ratio of 0.3505.

FIG. 5A shows a transform which may be applied to the mass spectral data resulting the determination of a value New X.

The equations which may be used for calculating New X are:

$$\text{New } X = (f_{m/z} - (t_d + b))/m \tag{1}$$

wherein $f_{m/z}$ is the fractional mass to charge ratio, $t_d$ is the ion mobility drift time, b is the y-intercept and m is the slope.

FIG. 5A shows a plot of count versus New X and the main peak as shown corresponds with ions having charge states of $2^+$, $3^+$, $4^+$, $5^+$ and $6^+$.

Figure 5B:
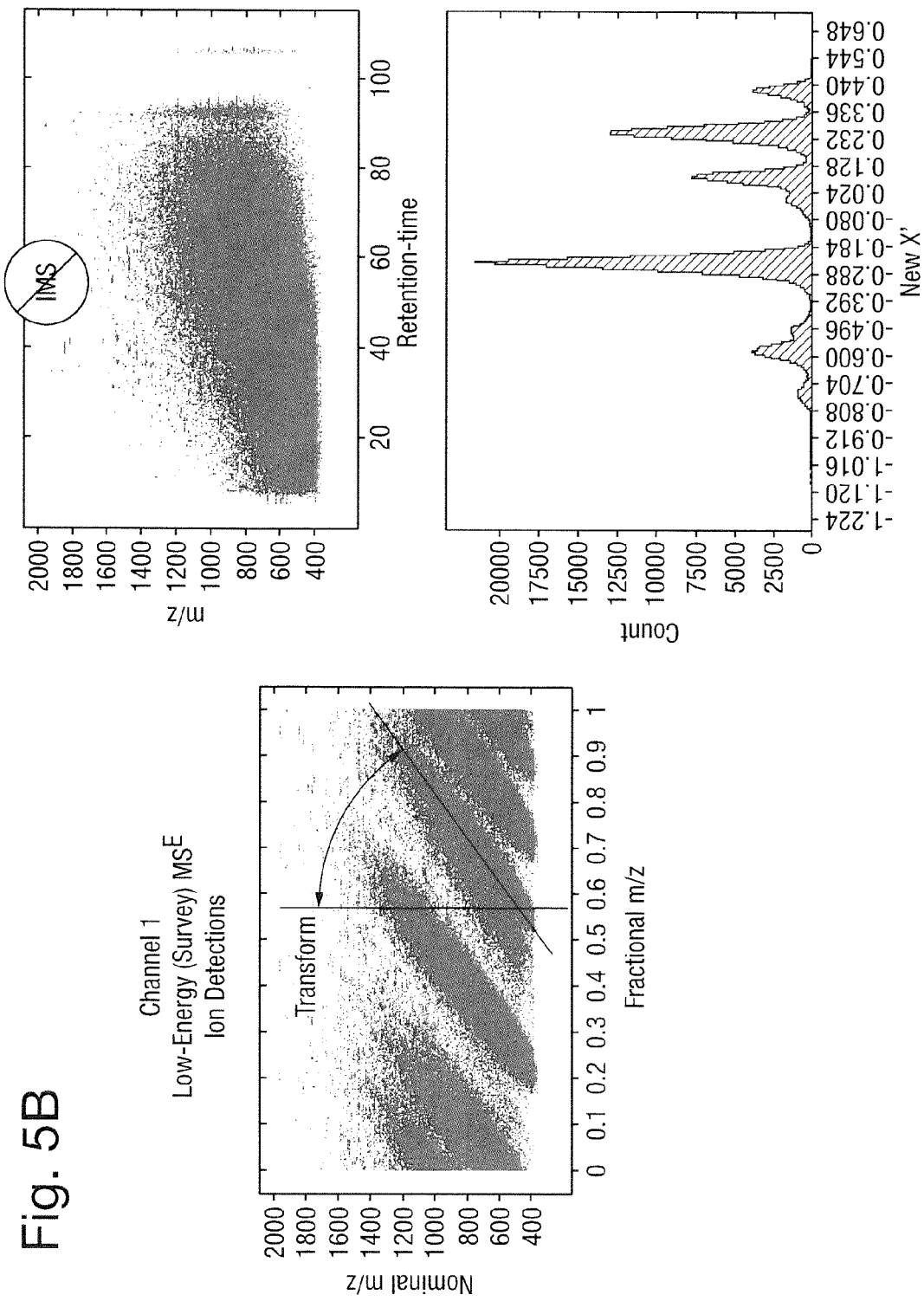
FIG. 5B shows a corresponding transformation which is applied if the ions are not subjected to ion mobility separation to determine a value of New X' and FIG. 5C shows both New X and New X' values.

The mass spectral data shown in FIG. 5A was obtained by subjecting the ions to ion mobility separation. However, embodiments may also apply to mass spectral data wherein the ions are not subjected to ion mobility separation. FIG. 5B shows low energy ion detections wherein the ions were not subjected to in mobility separation.

In the case that the ions are not subjected to ion mobility separation, then a similar transformation is applied using instead the integer or nominal mass to charge ratio in place of the ion mobility drift time in order to calculate a value New X':

$$\text{New } X' = (f_{m/z} - (N_{m/z} + b))/m \tag{2}$$

wherein $f_{m/z}$ is the fractional mass to charge ratio, $N_{m/z}$ is the integer or nominal mass to charge ratio, b is the y-intercept and m is the slope.

Figure 5C:
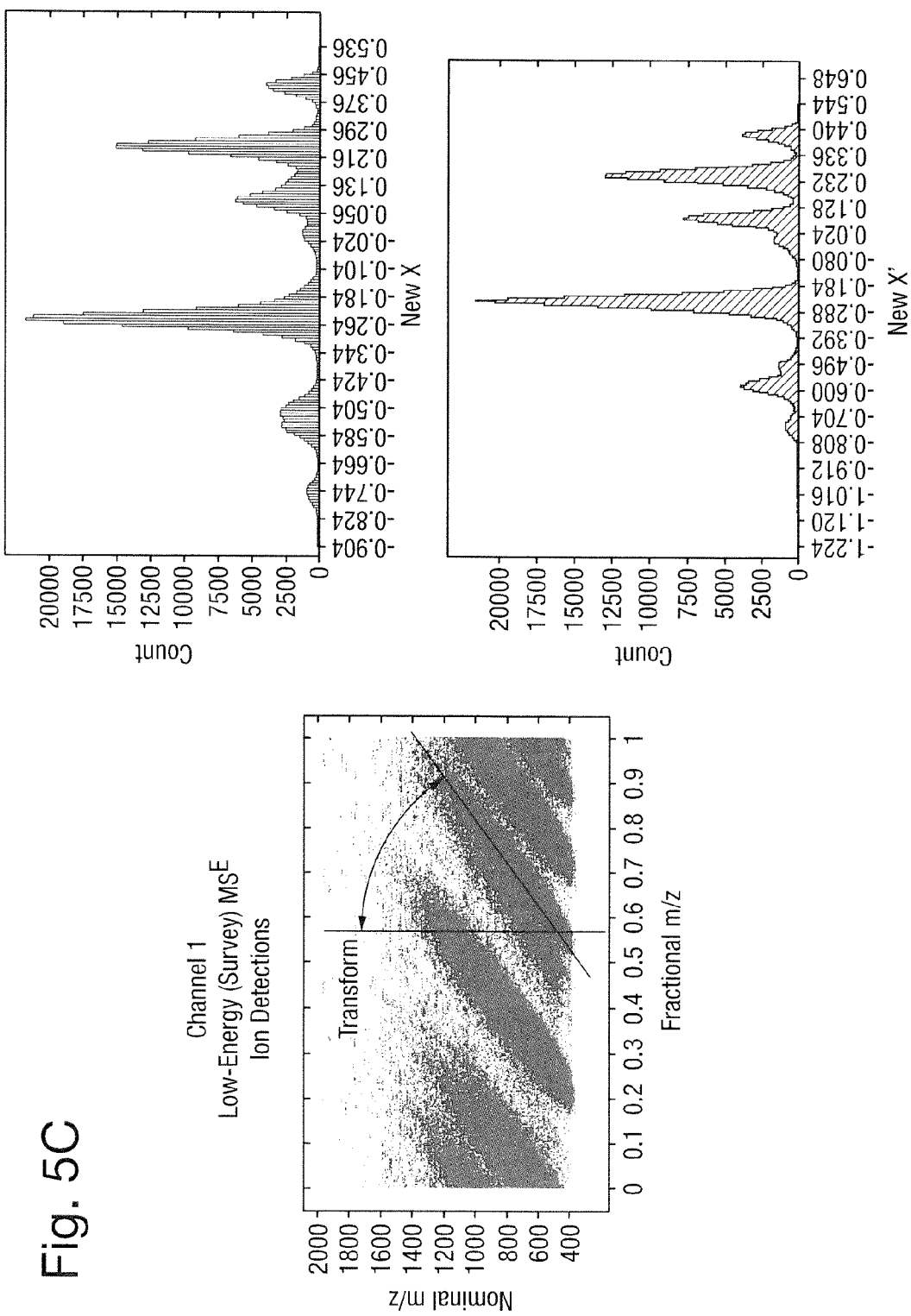

FIG. 5C shows that according to an embodiment values of New X and New X' may be determined since there are situations wherein the value of New X' may be used to determine the charge state of an ion if the determined value of New X does not result in an unique charge state determination.

A value Δ New X' may also be determined which represents the difference between the value New X' and the value New X.

The values New X and New X' may be calculated on-the-fly or during generation of charge state lookup tables from a SQL database containing the simulated proteomes, metabolomes or lipidomes in a manner as will be described in more detail below.

An example workflow according to an embodiment is illustrated in FIG. 6.

According to an embodiment a control sample may first be analysed and processed to both validate instrument performance as well as update models stored in a "Simulator" component of the processor in order to best reflect the experimental workflow. The step of analysing and processing a control sample is shown in both FIGS. 7 and 8.

A control sample comprising pre-digested *Escherichia coli* sample was analysed using the same analytical workflow as was followed with subsequent experiments. Prior to acquisition of the control sample, the proteome of the MC4100 strain of *Escherichia coli* was first processed by the "Simulator" component of the processor using a set of pre-loaded models.

The proteomics sample was then analysed and data was acquired and the resulting peptide identifications were optionally paired (experimental to simulated) by charge state and isotope number.

According to an embodiment the algorithm may then calculate a linear least squares fit models for both chromatographic retention time $t_r$ and ion mobility drift time $t_d$. With regards ion mobility drift time $t_d$ the algorithm may create individual models for each charge state z. Accordingly, the "Simulator" models are updated and adjusted for the subsequent experimental acquisitions.

Once the control sample has been run and the "Simulator" model adjusted, experimental data may then be acquired. As a first step, raw ion detections with their associated experimental attributes may be read into a charge determination and isotope clustering algorithm "Select3D" 10 as shown in FIG. 6. Processing may commence with the removal of any and all chemical noise. The process of removing chemical noise is illustrated in FIG. 3 and is described in more detail above.

In a second loop the raw ion detections may then be sorted into two groups, $1^+$ and $>1^+$ (as illustrated by FIG. 2). The $>1^+$ group may then be sorted by ion area in descending order up to a user or algorithmically derived maximum ion count. All the ions exceeding the max count may be removed from further processing. The selected ions may then be sorted by mass to charge ratio in ascending order.

Next a series of user-defined or algorithmically derived match tolerances for mass to charge ratio, chromatographic retention time $t_r$ and ion mobility drift time $t_d$ may be applied to determine each ions' possible charge state connections. Typically these values are set as a fraction of each attributes' value at half-height.

For example, tolerances $\Delta t_r$, $\Delta t_d$ and $\Delta m/z$ may be set to a fractional value of 0.5, 1 and 0.66 of FWHM respectively according to an embodiment.

A charge state connection may be confirmed if a companion ion is found illustrating the appropriate mass to charge ratio tolerance $\Delta$ m/z (1/z, from $z_{max\ to\ z=2}$) within the previously described match tolerances of chromatographic retention time $t_r$ and ion mobility drift time $t_d$.

Charge state connections will be utilized later in the processing for further resolution of each ions charge state probability.

Once the input ion detections have been filtered and the charge state connections established the algorithm may then start a z-loop for ion chain construction 13. The z-loop begins with the lowest mass to charge ratio ion at the highest experimental charge state z. The mass to charge ratio tolerance $\Delta$ m/z (1/z) for the current z-loop may be added or applied and the algorithm may query 14 the remaining ion detections for a match within the applied match tolerances.

If an ion chain cannot be created in the current z loop, all ions may be released 15 and the algorithm may migrate to the next mass to charge ratio and the process may be repeated until a tentative ion chain is constructed.

Once a tentative ion chain is constructed, at this point the charge state is assumed (z-loop) and given ion selection is in order of mass to charge ratio ascending, then the first ion in the chain is assumed to relate to the $A_0$ ion.

Knowing both the charge state z and the mass to charge ratio of the $A_0$ ion, the algorithm may then calculate a molecular mass by using the elemental composition of an "averagine" (i.e. a theoretical amino acid) and a theoretical isotopic distribution 16 may be determined.

As previously described, the raw ion detections may be parsed into two charge groups ($1^+$, $>1^+$). The ions in each group may be limited by rank intensity (most-to-least) to a user-defined maximum precursor ion count. The lowest ranked precursor ion intensity (x2) may set the experimental limit of detection ("LOD"). With the calculated isotope model and limit of detection the algorithm may determine if the chain is viable by comparing the number of ions (L) in the chain to the number of ions predicted and if (L) is greater than or equal to the number predicted then the tentative ion chain passes the minimum length test and the process continues, otherwise the ions may be released and the algorithm may continue to the next mass to charge ratio.

Figure 7:
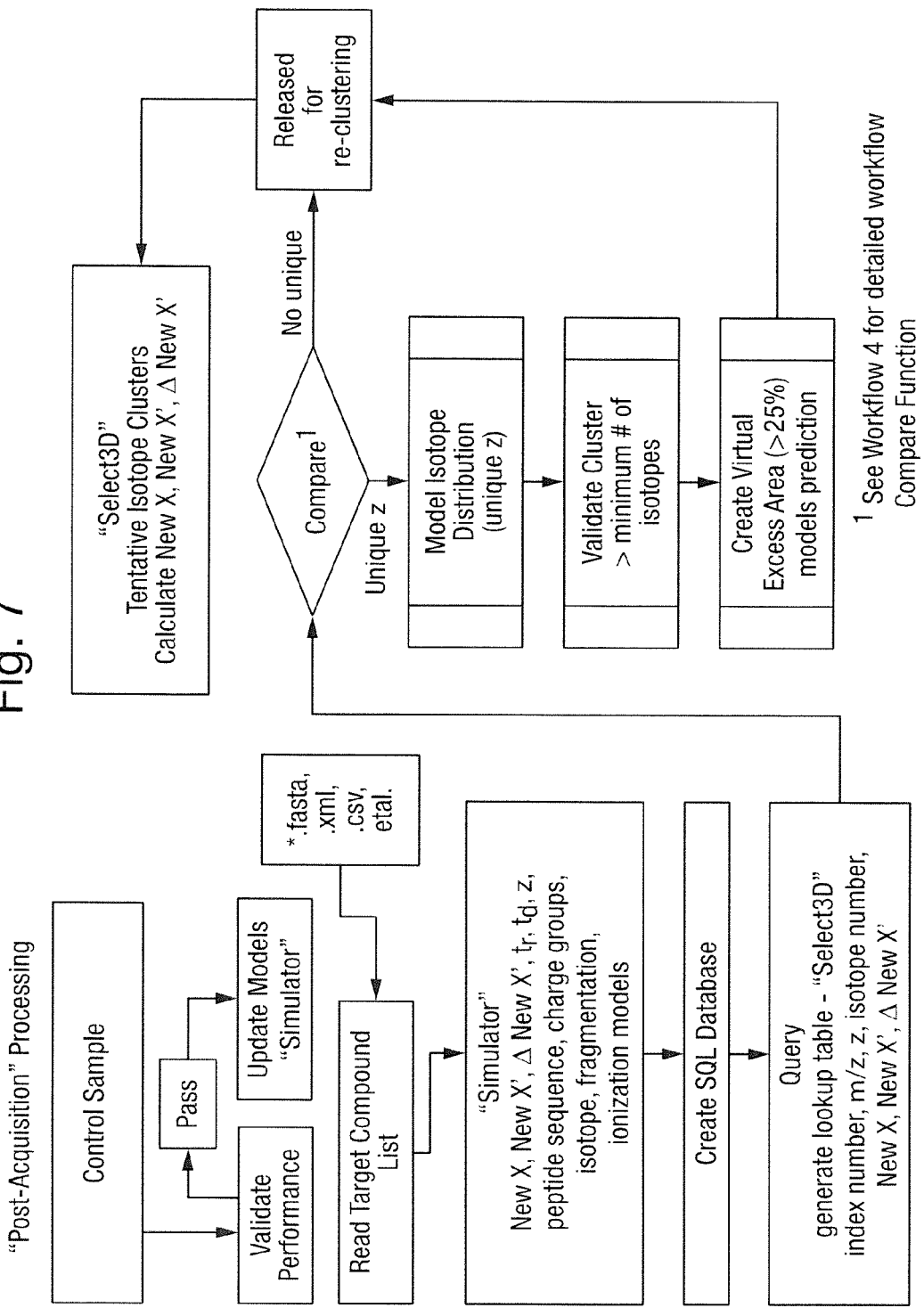
FIG. 7 shows the steps involved in post-acquisition processing.
Figure 8:
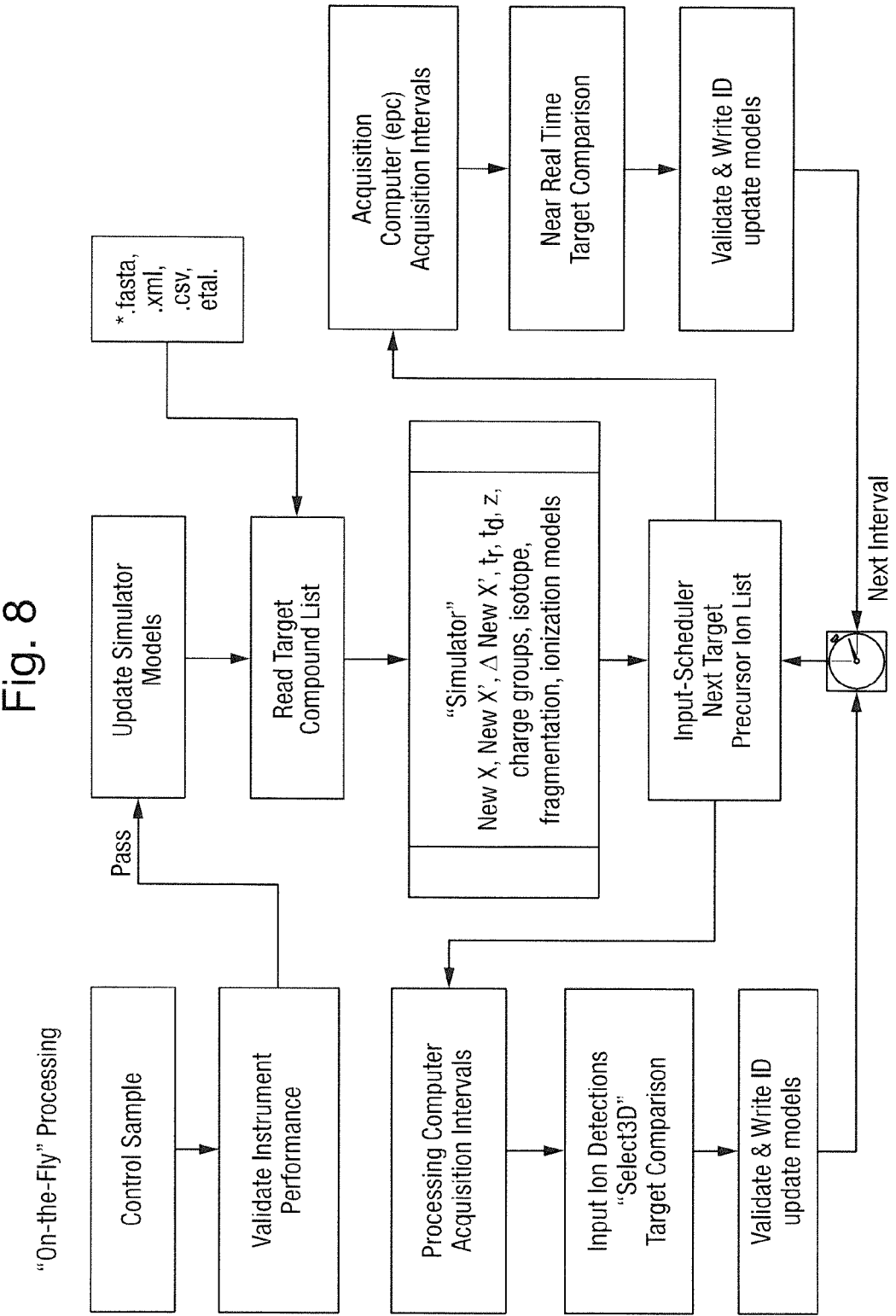
FIG. 8 shows the steps involved in on-the-fly processing.

FIG. 7 shows a post-acquisition processing flow diagram and FIG. 8 shows an on-the-fly processing flow diagram.

The complete process is illustrated and will be described in more detail with reference to FIGS. 9-15. When an initial ion chain passes the minimum number filter then a "Compare" portion of the algorithm may be activated.

Given a mass analysers' ability to accurately measure mass to charge ratio to within a few parts-per-million the algorithm may limit the mass to charge ratio tolerance $\Delta$ m/z range for querying the lookup table to each ions' width at half-height. The returned New X, New X' and Δ New' values are then distributed in 0.010 mass bins.

According to an embodiment the algorithm controls the bin width based on a minimum number of representative ions for calculating the charge state probabilities. Bins widths may also be user-definable. Once the bin widths have been set then the algorithm may calculate a simple distribution on the returned charge states and may determine the probability of each possible charge state 13.

In instances where New X does not return a charge state probability of 1 (i.e. an unique charge state), New X' and Δ New X' may be used as tie breakers.

According to an embodiment if the calculated charge state probability is less then unity, then a comparison may be made between the charge state connections and the New X charge state count. There will be instances where a transformed New X can exist at multiple charge states albeit, in the mass to charge ratio, chromatographic retention time $t_r$ and ion mobility drift time $t_d$ space queried for the creation of the tentative ion chain, no ion of that charge state is present hence the charge state connections comparison. Here, the charge state probability value may be altered to reflect the absence of the interfering ions exhibiting that charge state. If the charge state probability as yet has not reached unity then the chromatographic retention time $t_r$ may be used to further resolve the charge state ion count for that New X.

As the chromatographic retention time $t_r$ increases so does both mass and charge. Given the algorithms' knowledge of the target ions chromatographic retention time $t_r$ in a final attempt at establishing a unique charge state a user-defined or algorithmically derived retention time window may be applied and the charge state, count and probabilities may be re-calculated.

Algorithmically, the applied retention time window may be set to whichever is greater −20× the chromatographic retention time $t_r$ FWHM or 0.25× the total elution time. Though limited, even after all algorithmic attempts at achieving a uniform or unique charge state probability, there are mass to charge ratio values that can exist at multiple charge states. Given the elemental composition of biomolecules there is a near certitude that at least one isotope in an isotopic cluster will be isolated by charge state using high mass resolving power and/or chromatographic retention time $t_r$ and ion mobility drift time $t_d$. If there are no unique charge state ions in the constructed ion chain, then all ions may then be released 15 and the processing may continue to the next mass to charge ratio.

FIG. 9A shows a complete array comprising 2000 human proteins, 1,264,212 isotopes and 5 charge states over a range of New X from −0.992 through to 0.55042. Importantly, it should be understood that no mass to charge ratio tolerance has been applied i.e. all ions across the entire mass scale are represented.

Figure 9B:
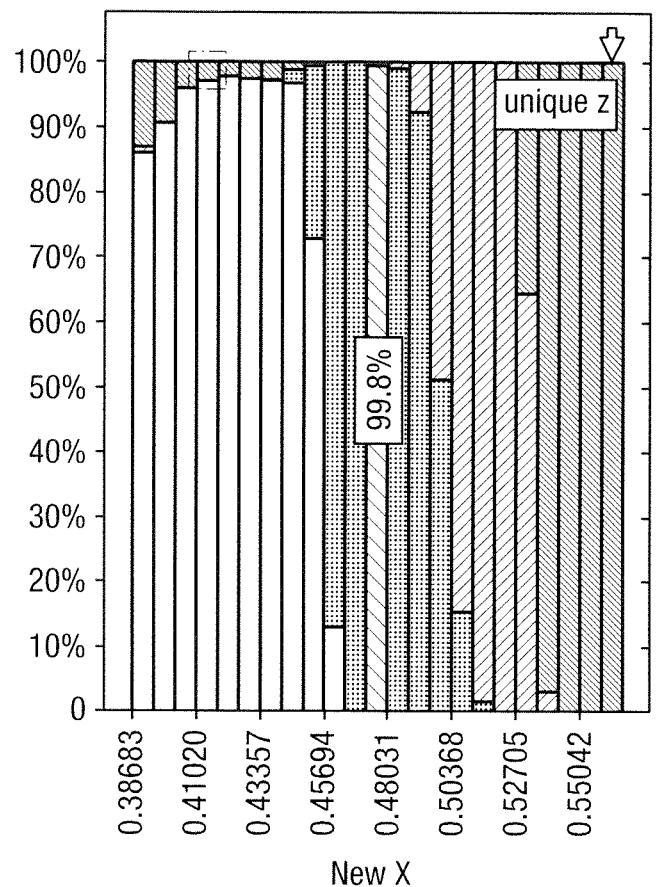
FIG. 9A shows a complete array comprising 2000 human proteins, 1,264,212 isotopes and 5 charge states and the distribution of charge states as a function of New X, FIG. 9B highlights a particular region of the distribution shown in FIG. 9A for values of New X between 0.38683 and 0.55042 and FIG. 9C highlights a particular region of the distribution shown in FIG. 9A for values of New X between −0.32206 and −0.213.

FIG. 9B shows in greater detail a portion of the array over a range of New X from 0.38683 to 055042. The different colours show the charge state and the length represents the percentage of all the ions illustrating the corresponding value of New X. Again, it should be emphasised that the percentage probability shown is in respect of all ions across the entire mass scale.

Even without applying a mass to charge ratio tolerance, it is apparent from FIG. 9B that ions having a value of New X around 0.55042 will have a 100% likelihood of having a charge state of $6^+$ i.e. these ions can be identified as having a unique charge state. Similarly, ions having a value of New X around 0.48031 will have a 99.8% likelihood of having a charge state of $4^+$ and a 0.2% likelihood of having a charge state of $5^+$ prior to the application of an additional requirement of having a mass to charge ratio within a certain tolerance.

Figure 9C:
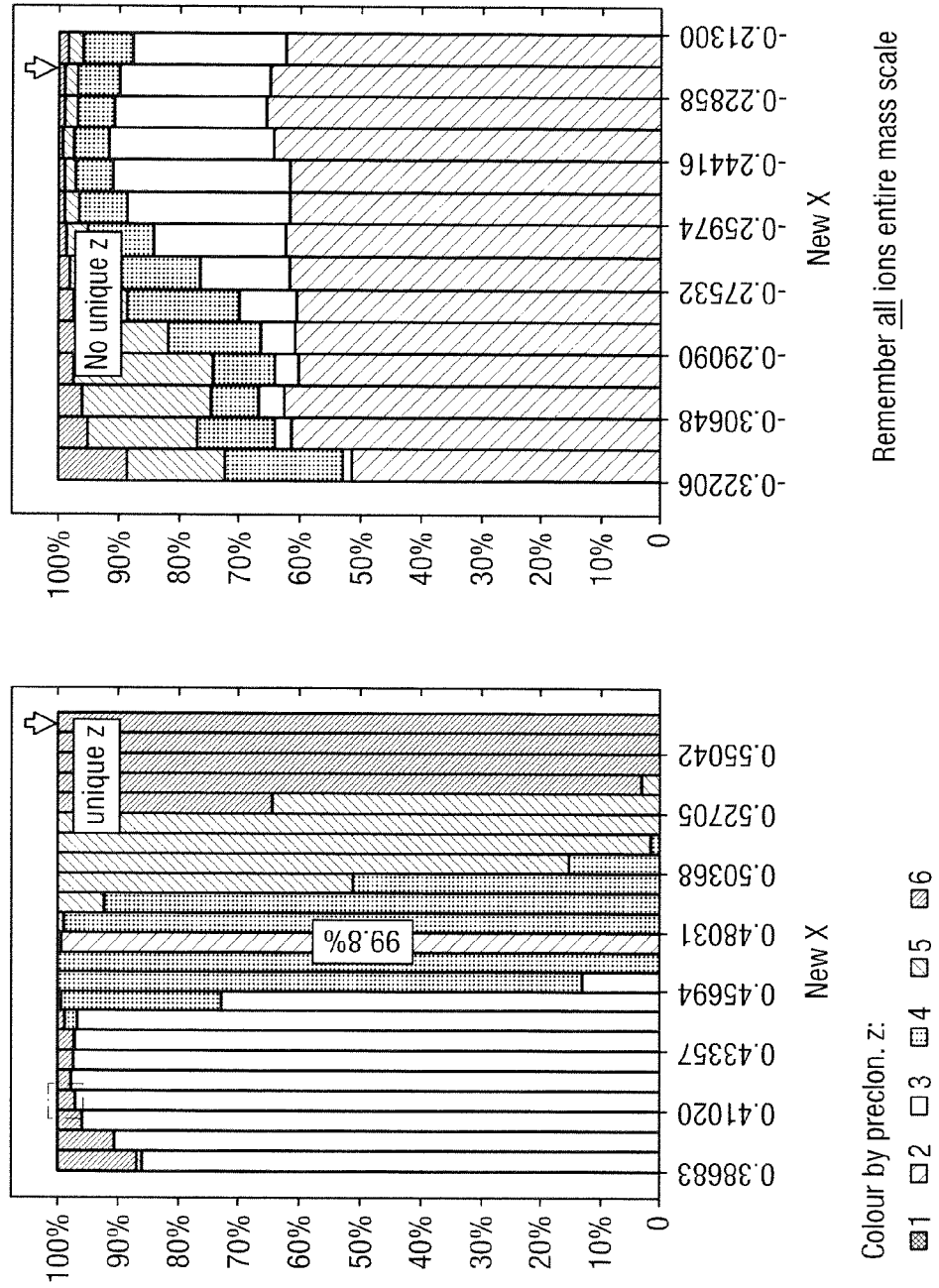

FIG. 9C illustrates another portion of the complete array corresponding to ions having a value of New X in the range from −0.32206 through to −0.213. It clear from FIG. 9C that ions in this range do not have a unique charge state, but again this is for ions across the entire mass range.

FIG. 10A shows inter-digitated $4^+$ and $3^+$ ion detections which would be particularly problematic for a conventional mass spectrometer to process but which may be correctly resolved according to embodiments. In the absence of prior knowledge a conventional de-isotoping algorithm may construct a $4^+$ ion cluster interpreting the ion having a mass to charge ratio of 549.3058 as being solely the $A_1$ isotope of an $A_0$ ion having a mass to charge ratio of 549.0398.

FIG. 10B illustrates how with the elimination of the 549.3058 ion a de-isotoping algorithm is unable to construct a correct $3^+$ charge cluster starting at mass to charge ratio 548.9784 but is able to create a (phantom) $3^+$ ion cluster starting at mass to charge ratio 549.6436. The first inset shown in FIG. 10O shows the mass to charge ratio and the ion mobility drift time of the 549.0398 ion. When the transformation is performed according to an embodiment then ions having a value of New X in the range −0.52482 through to −0.51536 have a 100% likelihood of having a charge state of $4^+$. It will be understood that in this case a mass to charge ratio tolerance (±50 mDa) is applied.

Figure 11:
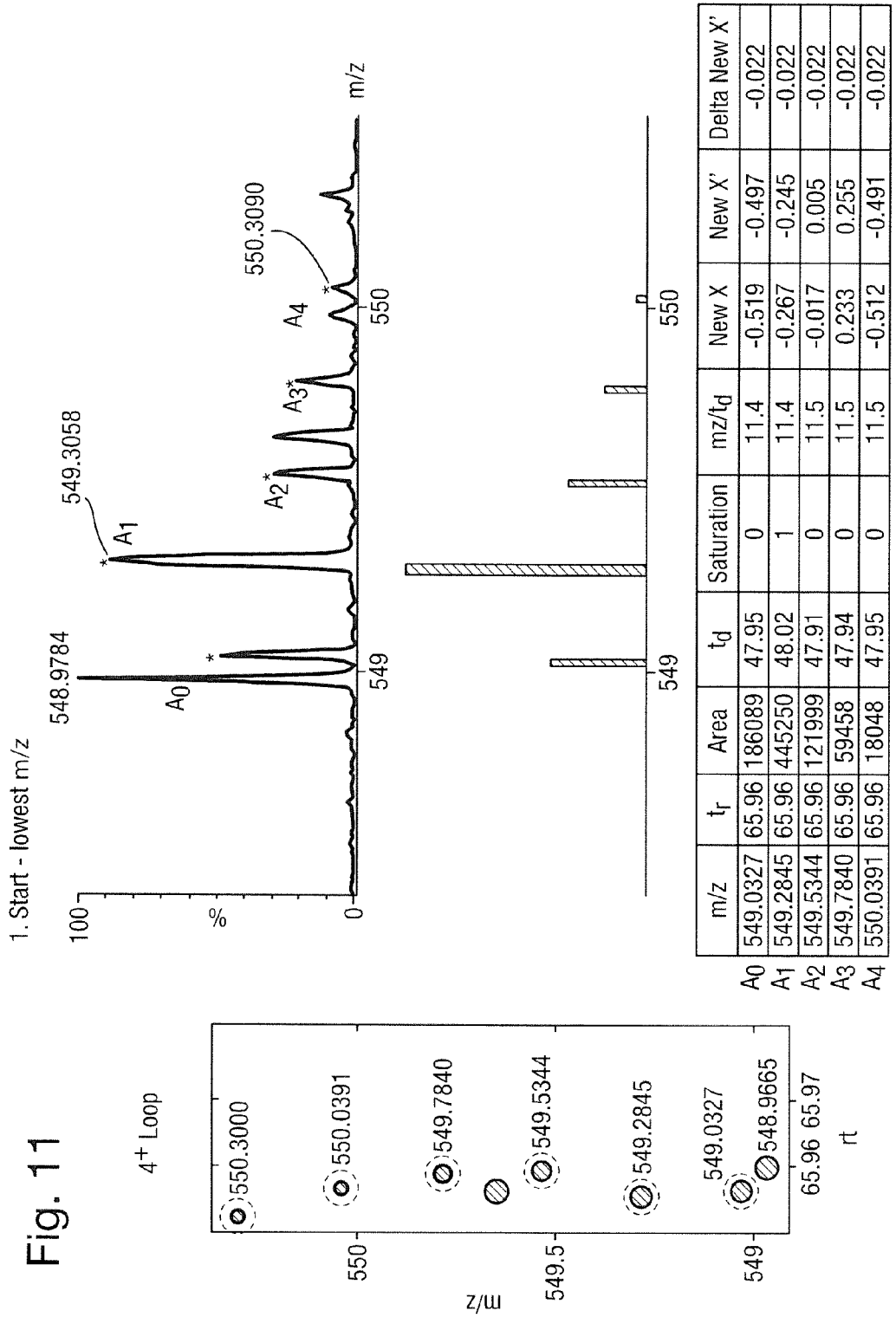
FIG. 11 shows a $4^+$ z-loop and illustrates the process of starting with ions having the lowest mass to charge ratio.

FIG. 11 illustrates a $4^+$ loop according to an embodiment. The $A_0$ ion is determined to have a mass to charge ratio of 549.0327 and the $A_1$ ion has a mass to charge ratio of 549.2845 but the intensity is too large (saturated). The $A_2$ ion has a mass to charge ratio of 549.5344, the $A_3$ ion has a mass to charge ratio of 549.7840 and the $A_4$ ion has a mass to charge ratio of 550.0391.

Figure 12:
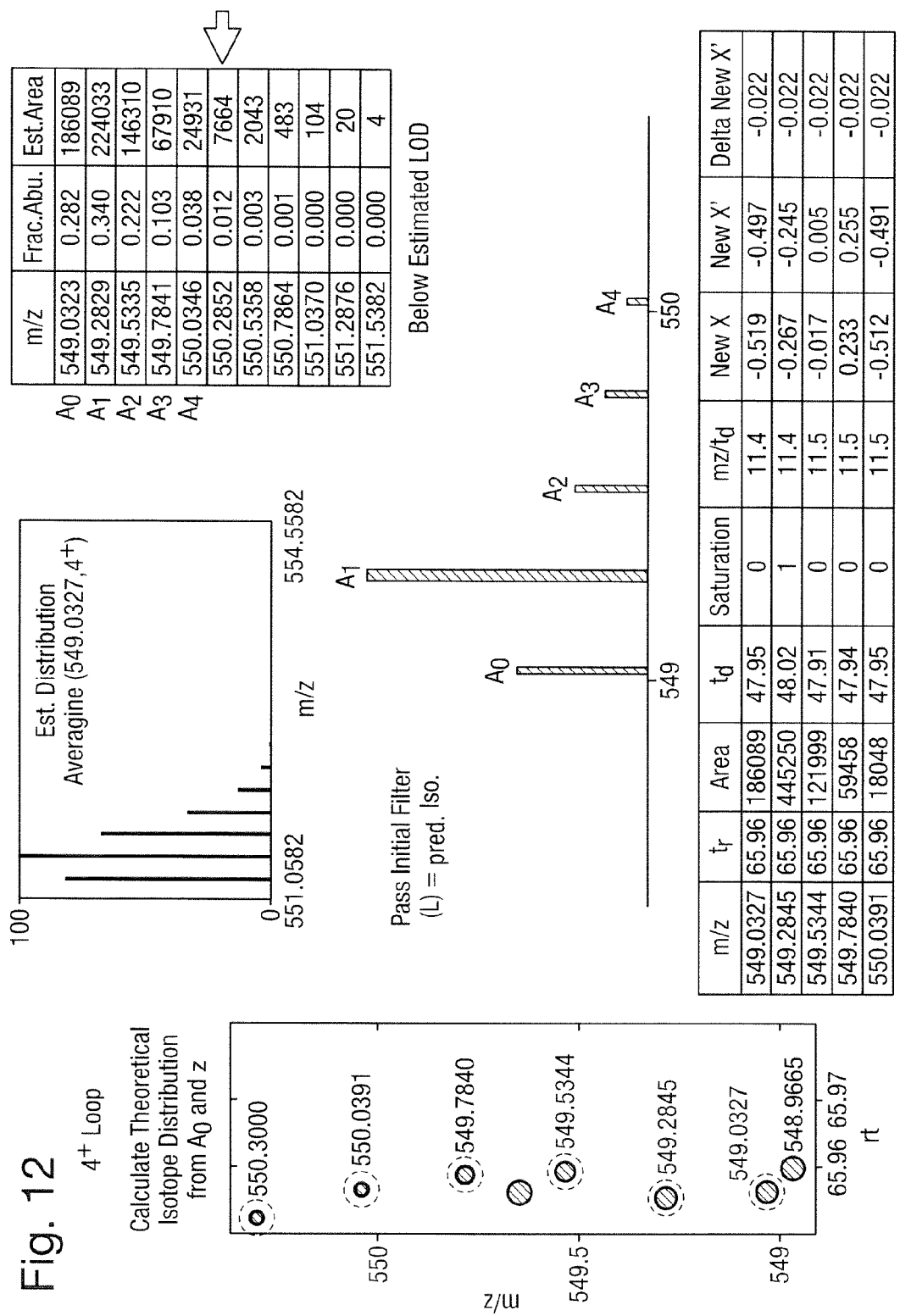
FIG. 12 shows a $4^+$ loop and illustrates the process of calculating a theoretical isotope distribution from $A_0$ and the determined charge state z.

FIG. 12 illustrates further the $4^+$ loop and shows the predicted or estimated isotopic distribution of a theoretical bio-molecule "Averagine" having a mass to charge ratio of 549.0327 and a $4^+$ charge state. In particular, the relative intensities of the $A_0$, $A_1$, $A_2$, $A_3$ and $A_4$ peaks are shown.

The inset in the top right of FIG. 12 shows further isotopic ions which are below the limit of detection ("LOD").

In particular, it is noted that from the theoretical distribution if the estimated area of the $A_0$ peak is 186089 then the estimated area of the $A_1$ peak is 224033. However, with the experimental data the $A_0$ peak has an area of 186089 but the $A_1$ peak has an area of 445250 i.e. approximately twice that predicted.

Figure 13:
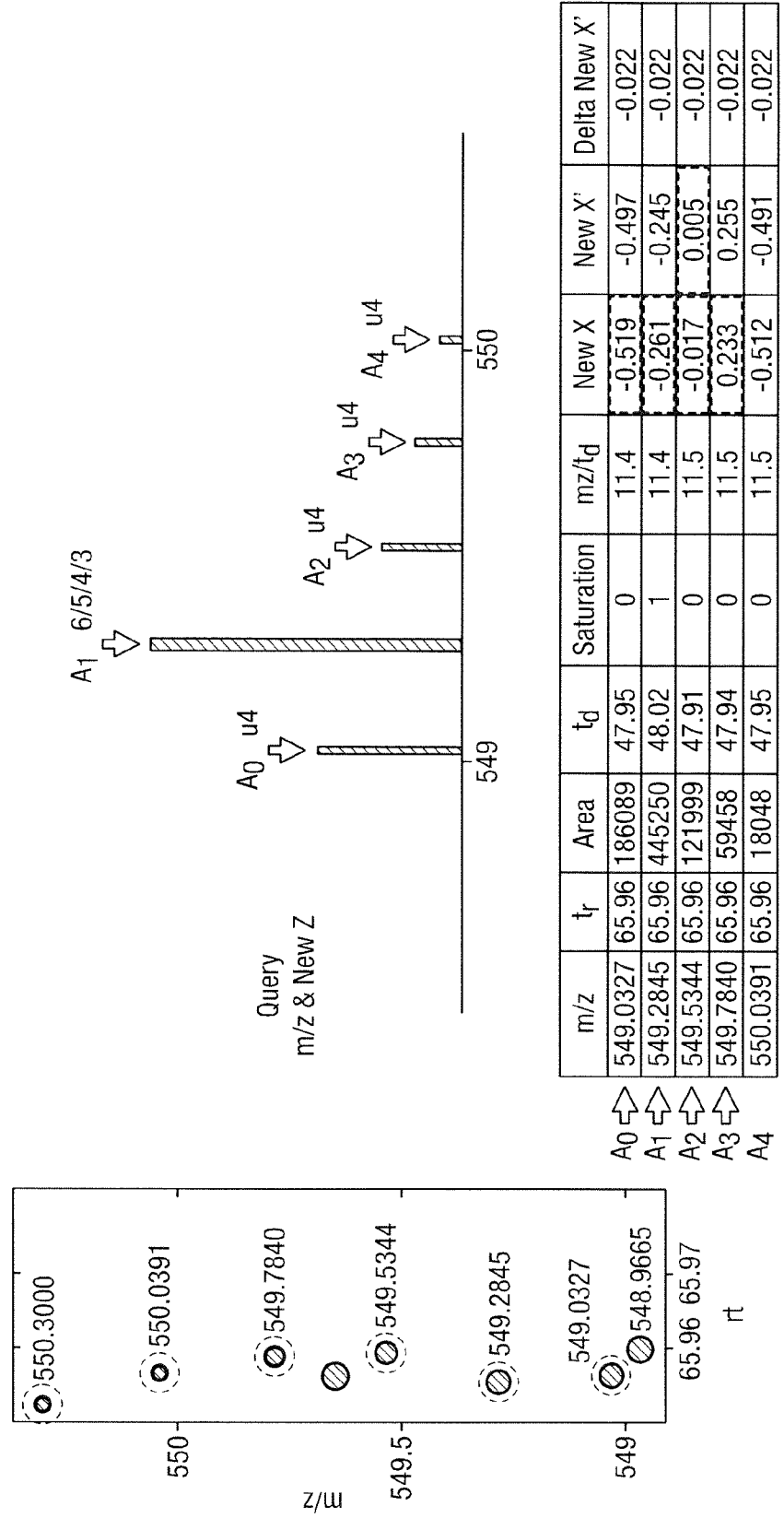
FIG. 13 shows a $4^+$ loop and illustrates the process of assigning charge state probabilities.

FIG. 13 shows the $4^+$ loop assigning charge state probabilities. The New X value relating to the $A_0$ ion having a mass to charge ratio of 549.0327 is −0.519 and the New X value uniquely identifies this ion as having a charge state of $4^+$. The $A_1$ ion has a mass to charge ratio of 549.2845 but the New X value of −0.267 corresponds with ions having charge states of $6^+$, $5^+$, $4^+$ and $3^+$ i.e. the charge state is not uniquely determined. The $A_2$ ion has a mass to charge ratio of 549.5344 and the New X value is −0.017 which corresponds with ions having a charge state of $4^+$ and $3^+$. However, the New X' value is 0.005 which uniquely identifies the ion as having a charge state of $4^+$. The $A_3$ ion has a mass to charge ratio of 549.7840 and the New X value uniquely identifies the ion as having a charge state of $4^+$.

FIG. 14 shows the $4^+$ loop and shows the process of creating a virtual ion when the area of an isotope peak exceeds that expected from a theoretical isotope distribution. From the theoretical isotopic distribution the $A_1$ ion should have an area of approximately 224033. However, the intensity of the $A_1$ ion was observed as being 445250. Accordingly, a virtual ion at mass to charge ratio of 549.2845 and having an intensity of 221217 (i.e. 445250 minus 224033) is created.

Figure 15:
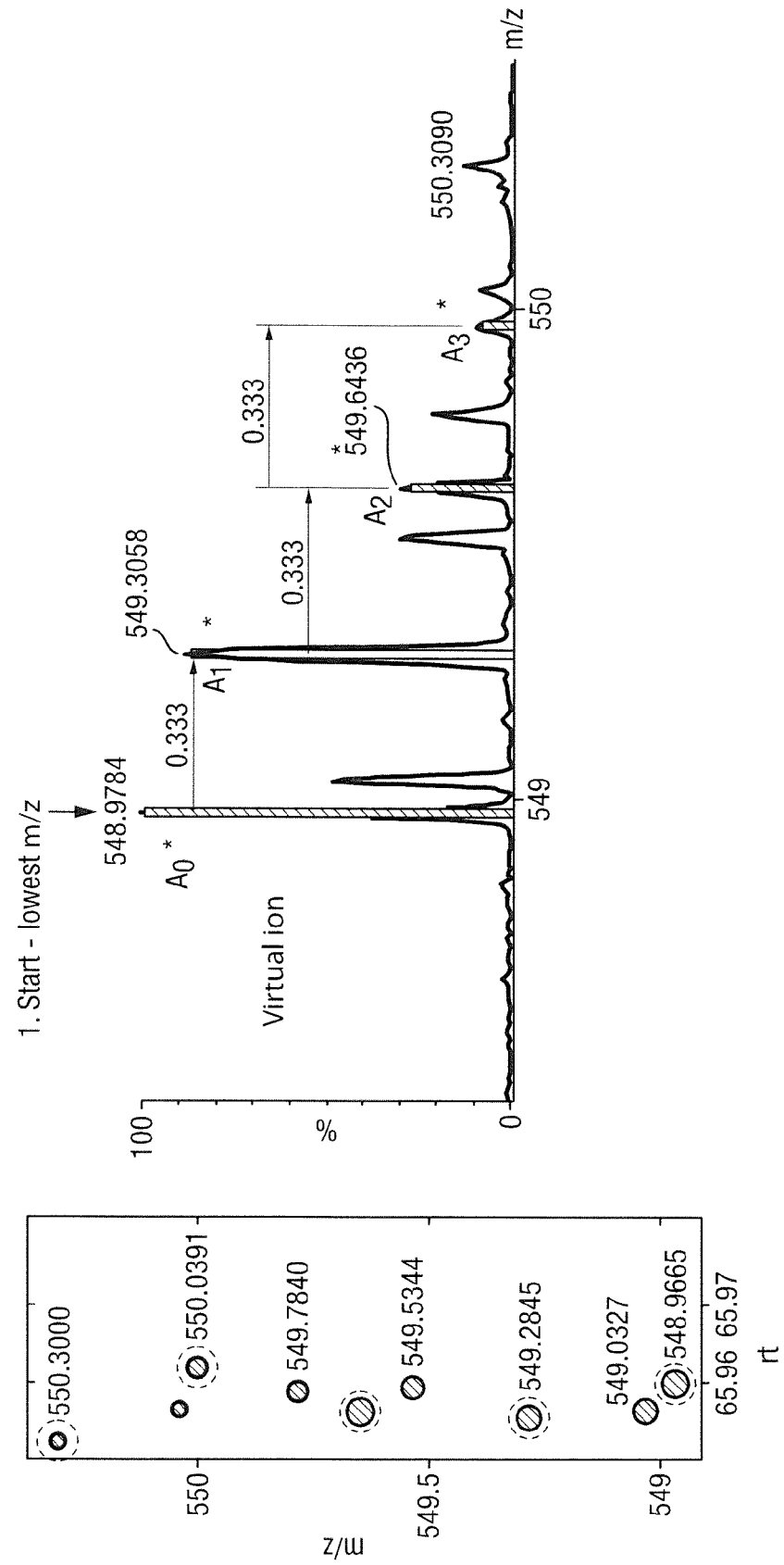
FIG. 15 shows a $3^+$ loop and illustrates the process of checking the ratio of the theoretical areas of the ion peaks to the experimentally determined ion peak areas.
Figure 15:
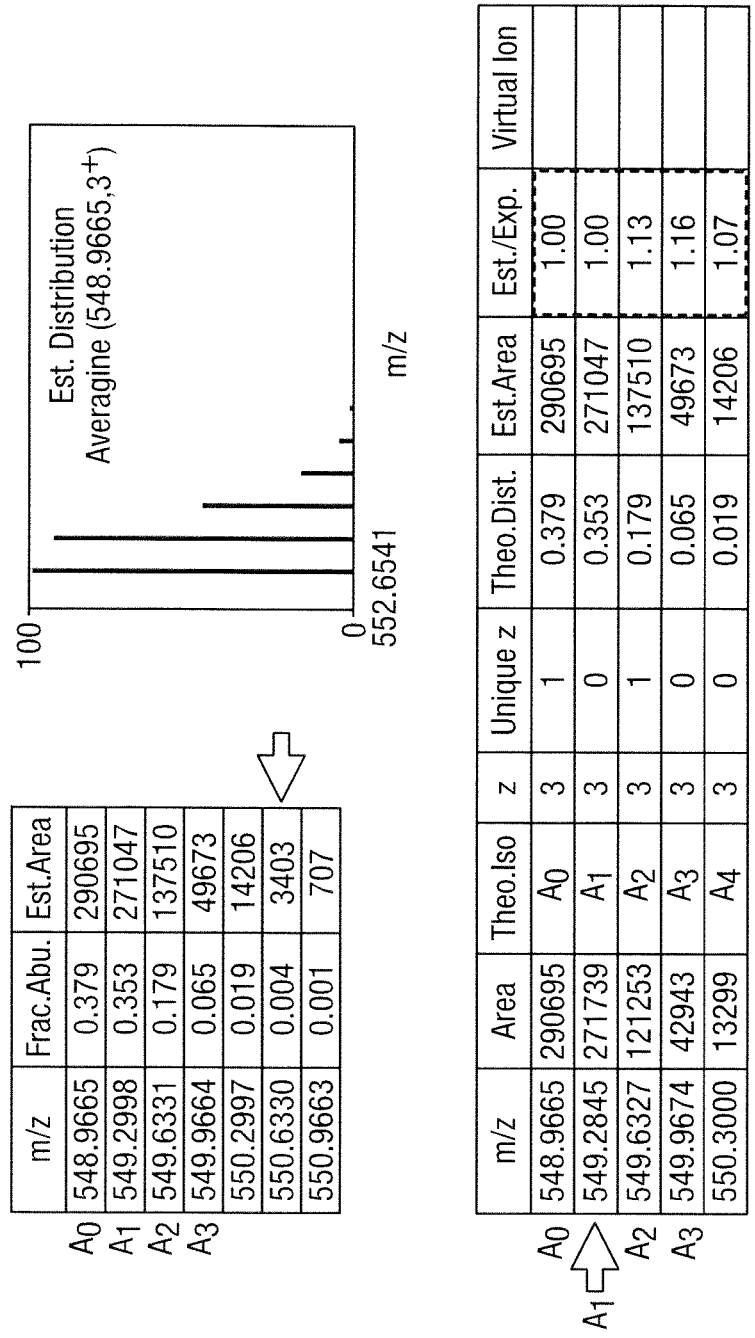

FIG. 15 shows the $3^+$ loop and illustrates the theoretical isotopic abundance of an ion having a mass to charge ratio of 548.9665 and a charge state of $3^+$. The theoretical or estimated areas of the ion peaks are in close agreement with the experimentally determined areas of the ion peaks.

FIG. 16 illustrates the problem of trying to determine where an isotope cluster starts and ends. An $A_0$ $3^+$ ion having a mass to charge ratio of 729.3981 and an intensity or area count of 37847 arbitrary area counts should theoretically have (just) three companion isotopes above the limit of detection. However, what the observed mass spectrum seemingly shows a chain of ten $3^+$ isotopes. In fact, what is shown in the mass spectrum shown in FIG. 16 is a series of inter-digitated $3^+$ nd $2^+$ charge clusters. It will be understood that conventional mass spectrometers will not be able to correctly process the inter-digitated charge clusters.

As illustrated in FIGS. 9-16 once a unique charge state has been identified and the ion chain passes the initial length validation test 17, the estimated sum area for the complete ion chain may be calculated by dividing the area of the lowest mass to charge ratio unique z ions' area by its corresponding theoretical abundance. This provides the means to compare the theoretical ion area to its corresponding experimental ion area in the form of a ratio.

If all ion area ratios are within the algorithmically determined tolerance (e.g. +/−25% of unity) then the ion chain is determined to be a valid isotope cluster.

If the ratio is less than unity by the allowed tolerance, then the experimental ions are considered to be interfered with and its area is adjusted by subtracting the area difference and a new virtual ion 18 may be created as illustrated in FIG. 14.

Conversely, if the ratio is greater than unity by the applied tolerance then the algorithm may re-calculate the summed area by pivoting off the next lowest mass to charge ratio ion illustrating a unique charge state. The area ratios may be recalculated and compared as previously described. This behaviour typically reflects either a series of inter-digitated ion clusters or a miss-assignment of the isotope number. Given that nature provides for stable isotopes (e.g. 0.01 of carbon is $^{13}C$) rarely, if ever, can the area of an isotope of a correctly constructed ion cluster be less than that predicted given its elemental composition.

Ion area ratios that are lower than what is predicted suggests that the ion used for calculating the estimated sum area may be a composite. An example of this behaviour is illustrated in FIG. 16 wherein five inter-digitated doubly charged ion clusters were algorithmically resolved into five distinct correctly distributed doubly charged ion clusters.

The ability to predict, with a high degree of certitude, the number of isotopes that should be associated to a charge cluster constructed from an ion of a given mass to charge ratio, charge state and area provides the means for the algorithm to create virtual $A_0$'s when the experimental limit of detection limits the ability to detect the true experimental $A_0$.

With respect to the natural distribution of stable isotope in nature, generally, this occurs most frequently on ions exhibiting higher charge state, lower intensity and higher mass to charge ratio. A lower intensity $5^+$ ion chain may be considered comprising of 4 ions. The algorithm assumes the lowest mass to charge ratio ion is the $A_0$. Given that the intensity ratio of near neighbours at high charge state and mass to charge ratio is much greater, incorrectly assigning $A_0$ leads to a significant over estimation of the summed area. This causes a severe ratio (theoretical/experimental) mismatch triggering the algorithm to re-index the isotope number from $A_0$ to $A_1$. As such, if the new area ratio is within the accepted tolerance a virtual $A_0$ is created with its area set to the theoretical. It follows as mass resolving increase the maximum number of discernible charge states will increase in concordance. Given that the algorithm, at the onset, establishes the experimental mass resolution it determines a maximum number of re-indexing attempts.

There are a number of avenues that can be algorithmically pursued once an isotope cluster has been validated. In contrast to a typical qualitative analysis whereby a product ion spectra from either a precursor isolation window (DDA) or time and/or time and drift aligned ($MS^E$ or $HD-MS^E$) is queried against a database, according to an embodiment the calculated exact mass to charge ratio, the chromatographic retention time $t_r$ and the ion mobility drift time $t_d$ may be queried directly against a SQL database of target compounds. Product ion spectra from candidate peptide sequences may be generated in a rapid manner and may be directly compared to the product ions illustrating the same chromatographic retention time $t_r$ and ion mobility drift time $t_d$ of the queried $A_0$. This can be accomplished in real time or post-acquisition as illustrated in FIGS. 7 and 8 respectively.

In experiments where a Target Compound List ("TCL") is included in the experimental workflow the Target Compound List is processed in the "Simulator" (running the updated models) and all target compounds are annotated with their retention time (and if ion mobility separation is employed then ion mobility drift times), charge-states, isotope distributions, ionization rank order, fragmentation pattern, New X, New X' and Δ New X'.

Although the present invention has been described with reference to various embodiments, it will be understood by those skilled in the art that various changes in form and detail may be made without departing from the scope of the invention as set forth in the accompanying claims.

The invention claimed is:

1. A method of mass spectrometry comprising:
ionising a sample and obtaining mass spectral data relating to a plurality of ion detection events;
applying match tolerances for mass to charge ratio and at least one of chromatographic retention time and ion mobility drift time to said ion detection events in order to determine possible charge state connections;
constructing a tentative isotope chain and querying ion detection events for a match to said tentative isotope chain;
wherein once a tentative isotope chain has been constructed, said method further comprises:
determining a corresponding theoretical molecular mass and a corresponding theoretical isotopic distribution;
querying one or more lookup tables and returning one or more parameters related to a fractional mass to charge ratio and at least one of: ion mobility drift time and nominal mass to charge ratio of said ion detection events; and
using said one or more parameters to determine a unique charge state of said ions.

2. A method as claimed in claim 1, further comprising analysing and processing a control sample prior to analysing said sample in order to validate instrument performance or update a simulation model.

3. A method as claimed in claim 1, further comprising parsing said ion detection events into a first group comprising singly charged ions and a second group comprising multiply charged ions.

4. A method as claimed in claim 1, wherein the step of applying a tolerance for chromatographic retention time comprises setting a tolerance at a fraction or percentage of the chromatographic retention time at the full width half maximum of a retention time peak.

5. A method as claimed in claim 1, wherein the step of applying a tolerance for mass to charge ratio comprises setting a tolerance at a fraction or percentage of the mass to charge ratio at the full width half maximum of a mass to charge ratio peak.

6. A method as claimed in claim 1, wherein the step of applying a tolerance for ion mobility drift time comprises setting a tolerance at a fraction or percentage of the ion mobility drift time at the full width half maximum of an ion mobility peak.

7. A method as claimed in claim 1, wherein a possible charge state connection is confirmed if a companion ion is located having at least one of a mass to charge ratio, a chromatographic retention time and an ion mobility drift time within said tolerances.

8. A method as claimed in claim 1, wherein the step of constructing a tentative isotope chain further comprises initially selecting an ion detection event having the lowest mass to charge ratio and the highest charge state.

9. A method as claimed in claim 1, wherein once a tentative isotope chain has been constructed then the first ion in said isotope chain and having a charge state is assumed to correspond with an $A_0$ ion.

10. A method as claimed in claim 1, further comprising comparing the number of ions in a tentative isotope chain to a predicted number of ions.

11. A method as claimed in claim 1, wherein the step of querying said lookup table further comprises limiting the mass to charge ratio range to the full width half maximum of a mass to charge ratio peak.

12. A method as claimed in claim 1, further comprising transforming the fractional mass to charge ratio and ion mobility drift time of ion detection events to determine a first parameter.

13. A method as claimed in claim 1, further comprising transforming the fractional mass to charge ratio and nominal mass to charge ratio of ion detection events to determine a second parameter.

14. A method as claimed in claim 1, wherein said one or more parameters are calculated during the generation of said one or more lookup tables.

15. A method as claimed in claim 1, wherein said one or more lookup tables are derived from a database of biomolecules or molecules of biological origin.

16. A method as claimed in claim 1, wherein said method further comprises distributing said one or more parameters amongst a plurality of mass or mass to charge ratio bins.

17. A method as claimed in claim 1, wherein if the use of one of said parameters is insufficient to determine a unique charge state of said ions then said method further comprises using another of said parameters to determine a unique charge state of said ions.

18. A method as claimed in claim 1, wherein if a unique charge state for said ions cannot be determined then said tentative isotope chain is no longer considered to represent a tentative isotope chain.

19. A method as claimed in claim 1, wherein once a unique charge state of said ions has been determined said method further comprises estimating a summed area for the complete isotope chain.

20. A mass spectrometer comprising:
an ion source for ionising a sample;
an ion detector system for obtaining mass spectral data relating to a plurality of ion detection events; and
a control system arranged and adapted:
(i) to apply match tolerances for mass to charge ratio and at least one of: chromatographic retention time and ion mobility drift time to said ion detection events in order to determine possible charge state connections;
(ii) to construct a tentative isotope chain and to query ion detection events for a match to said tentative isotope chain;
wherein once a tentative isotope chain has been constructed, said control system is further arranged and adapted:
(iii) to determine a corresponding theoretical molecular mass and a corresponding theoretical isotopic distribution;
(iv) to query one or more lookup tables and to return one or more parameters related to a fractional mass to charge ratio and at least one of ion mobility drift time and nominal mass to charge ratio of said ion detection events; and
(v) to use said one or more parameters to determine a unique charge state of said ions.

* * * * *